(12) United States Patent
Abraham

(10) Patent No.: US 8,403,859 B2
(45) Date of Patent: *Mar. 26, 2013

(54) IMAGE GUIDED CATHETERS AND METHODS OF USE

(75) Inventor: Theodore P. Abraham, Baltimore, MD (US)

(73) Assignee: Perceptive Navigation LLC, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/871,282

(22) Filed: Oct. 12, 2007

(65) Prior Publication Data

US 2008/0091104 A1  Apr. 17, 2008

Related U.S. Application Data

(60) Provisional application No. 60/851,451, filed on Oct. 12, 2006.

(51) Int. Cl.
*A61B 8/14* (2006.01)

(52) U.S. Cl. ........ 600/466; 600/462; 600/464; 600/437; 600/467; 600/407

(58) Field of Classification Search .......... 600/427, 600/478, 567, 462; 604/19; 128/772
See application file for complete search history.

(56) References Cited

U.S. PATENT DOCUMENTS

| | | | |
|---|---|---|---|
| 3,556,079 A | 1/1971 | Omizo | |
| 4,092,867 A * | 6/1978 | Matzuk | 73/609 |
| 4,869,258 A | 9/1989 | Hetz | |
| 5,106,368 A * | 4/1992 | Uldall et al. | 604/43 |
| 5,159,931 A | 11/1992 | Pini | |
| 5,181,514 A | 1/1993 | Solomon et al. | |
| 5,454,373 A | 10/1995 | Koger et al. | |
| 5,505,088 A | 4/1996 | Chandraratna et al. | |
| 5,509,909 A * | 4/1996 | Moy | 604/540 |
| 5,701,901 A | 12/1997 | Lum et al. | |
| 5,704,361 A | 1/1998 | Seward | |
| 5,967,984 A | 10/1999 | Chu et al. | |
| 5,997,497 A | 12/1999 | Nita et al. | |
| 6,068,638 A | 5/2000 | Makower | |
| 6,149,598 A | 11/2000 | Tanaka | |
| 6,162,179 A | 12/2000 | Moore | |
| 6,306,097 B1 | 10/2001 | Park et al. | |
| 6,572,551 B1 | 6/2003 | Smith et al. | |

(Continued)

FOREIGN PATENT DOCUMENTS

CA   2 376 103   3/2001

OTHER PUBLICATIONS

International Search Report corresponding to International Application No. PCT/US2007/081185 dated Jul. 10, 2008.

(Continued)

*Primary Examiner* — Jacqueline Cheng
*Assistant Examiner* — Joel F Brutus
(74) *Attorney, Agent, or Firm* — Cameron LLP

(57) ABSTRACT

An interventional medical device is provided that incorporates a forward-directed ultrasound imaging system integrated into a single device. The medical device can be in the form of sheaths, catheters, and interventional devices, particularly those suitable for minimally invasive procedures in the human or other mammalian body. The imaging system comprises one or more small ultrasound transducers that can be permanently integrated into the device or integrated into an interchangeable ultrasound transducer that can be inserted into and removed from the device to customize the device for a particular use. An ultrasound system can be provided in the device either alone or in combination with fiber optic imaging to provide a range of imaging and therapeutic capabilities of the device.

26 Claims, 32 Drawing Sheets

U.S. PATENT DOCUMENTS

| | | | |
|---|---|---|---|
| 6,582,390 B1* | 6/2003 | Sanderson | 604/19 |
| 6,592,559 B1 | 7/2003 | Pakter et al. | |
| 6,685,648 B2 | 2/2004 | Flaherty et al. | |
| 6,689,062 B1 | 2/2004 | Mesallum | |
| 7,100,614 B2 | 9/2006 | Stevens et al. | |
| 7,270,534 B2 | 9/2007 | Laar et al. | |
| 7,488,289 B2 | 2/2009 | Suorsa et al. | |
| 7,713,190 B2 | 5/2010 | Brock et al. | |
| 7,860,555 B2 | 12/2010 | Saadat | |
| 2001/0023323 A1* | 9/2001 | Nishtala et al. | 600/567 |
| 2002/0123698 A1* | 9/2002 | Garibotto et al. | 600/585 |
| 2003/0229286 A1* | 12/2003 | Lenker | 600/462 |
| 2004/0015193 A1* | 1/2004 | Iamson et al. | 607/9 |
| 2005/0090709 A1 | 4/2005 | Okada et al. | |
| 2005/0143664 A1* | 6/2005 | Chen et al. | 600/478 |
| 2006/0106315 A1 | 5/2006 | Edens | |
| 2007/0293724 A1* | 12/2007 | Saadat et al. | 600/156 |

OTHER PUBLICATIONS

Non-final Office Action issued Oct. 13, 2011 in U.S. Appl. No. 12/285,779 related by subject matter to the present application.
European Examination Report issued Apr. 26, 2012.

* cited by examiner

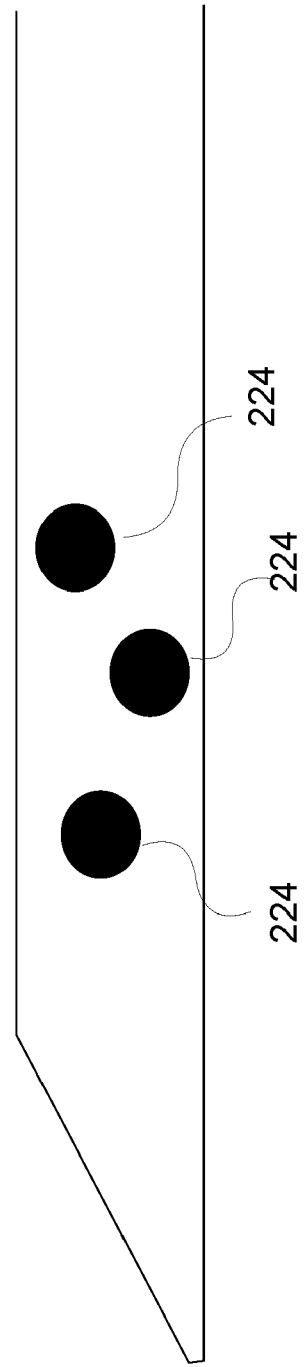
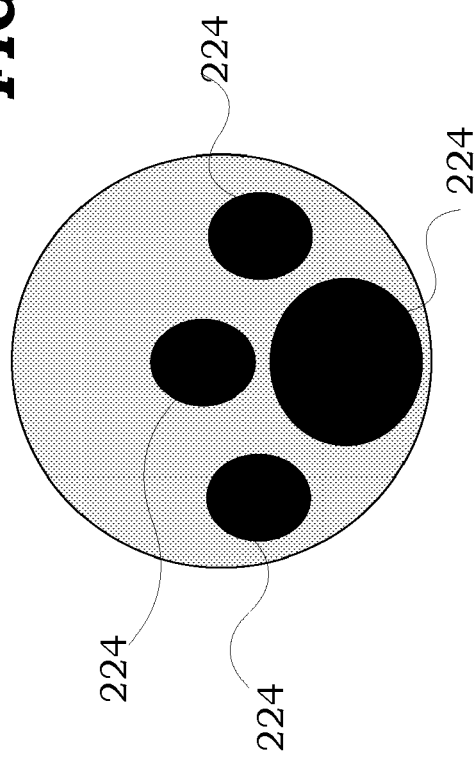

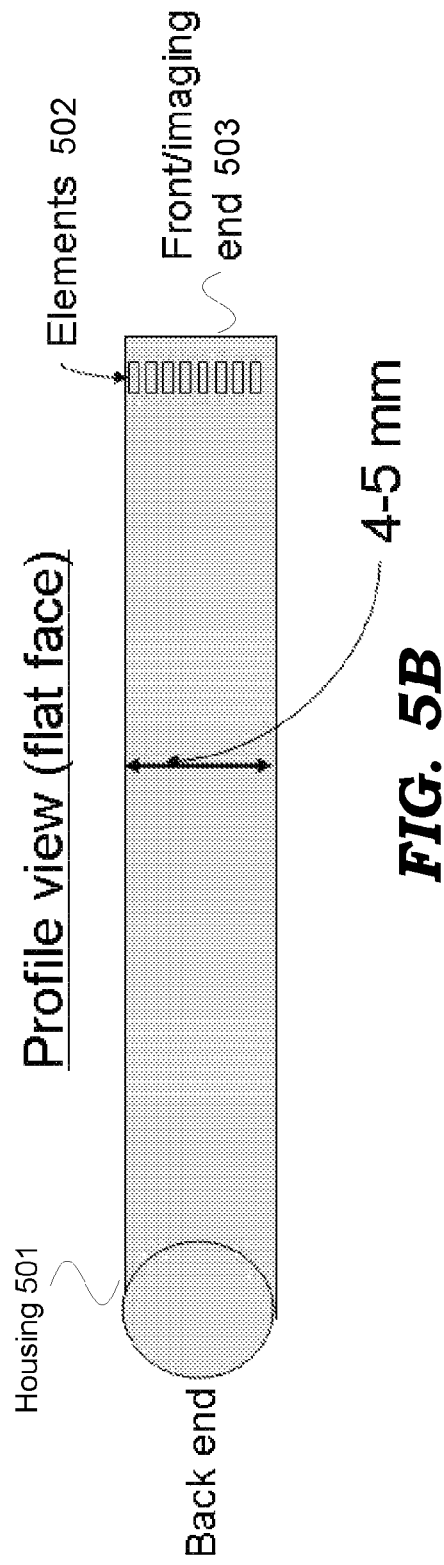
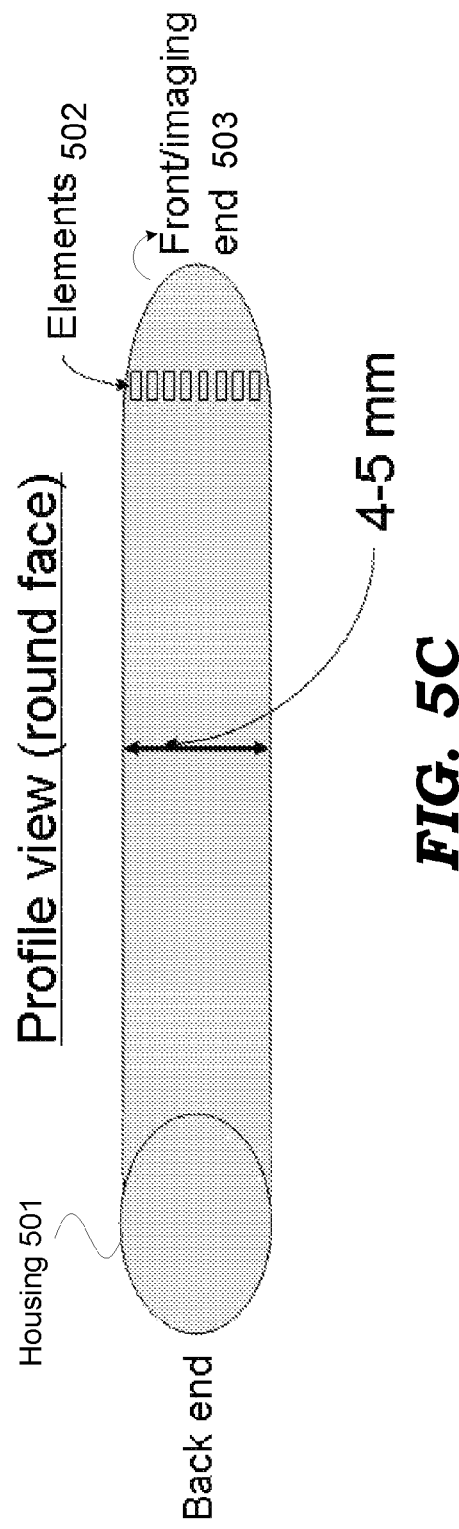

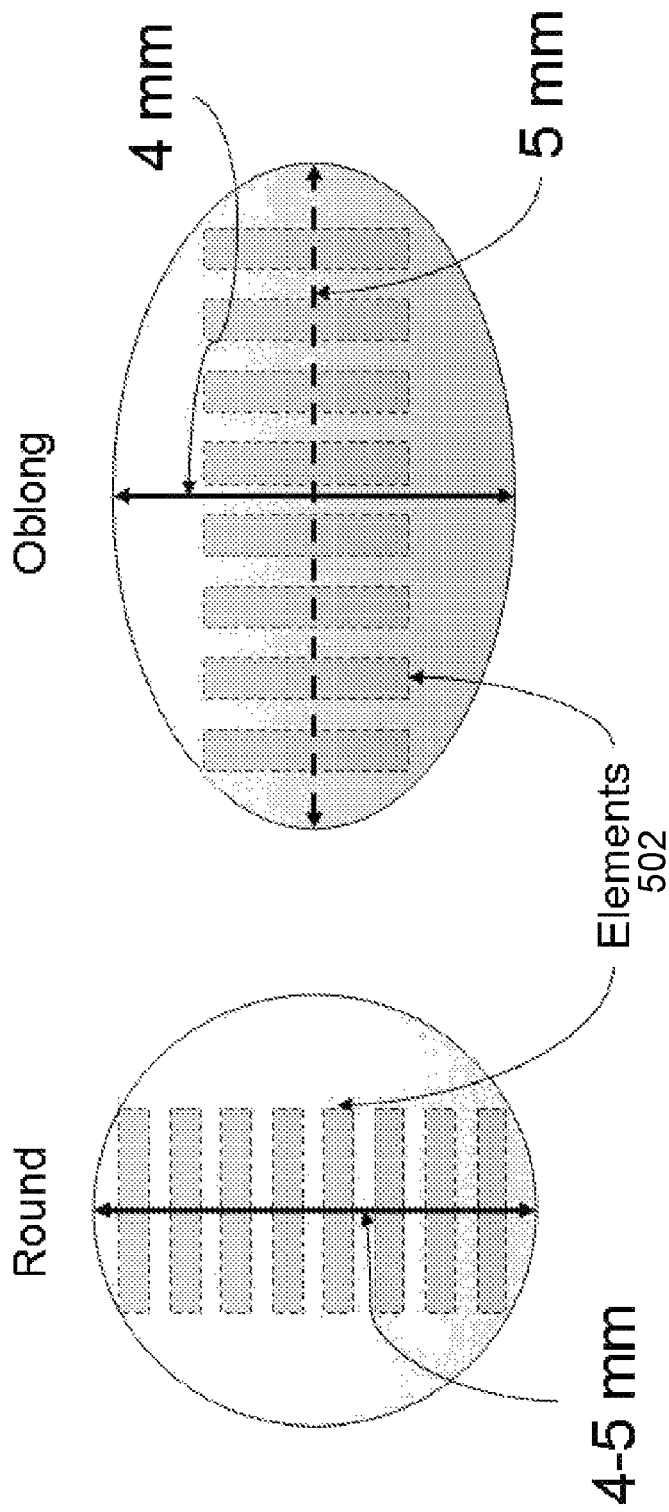

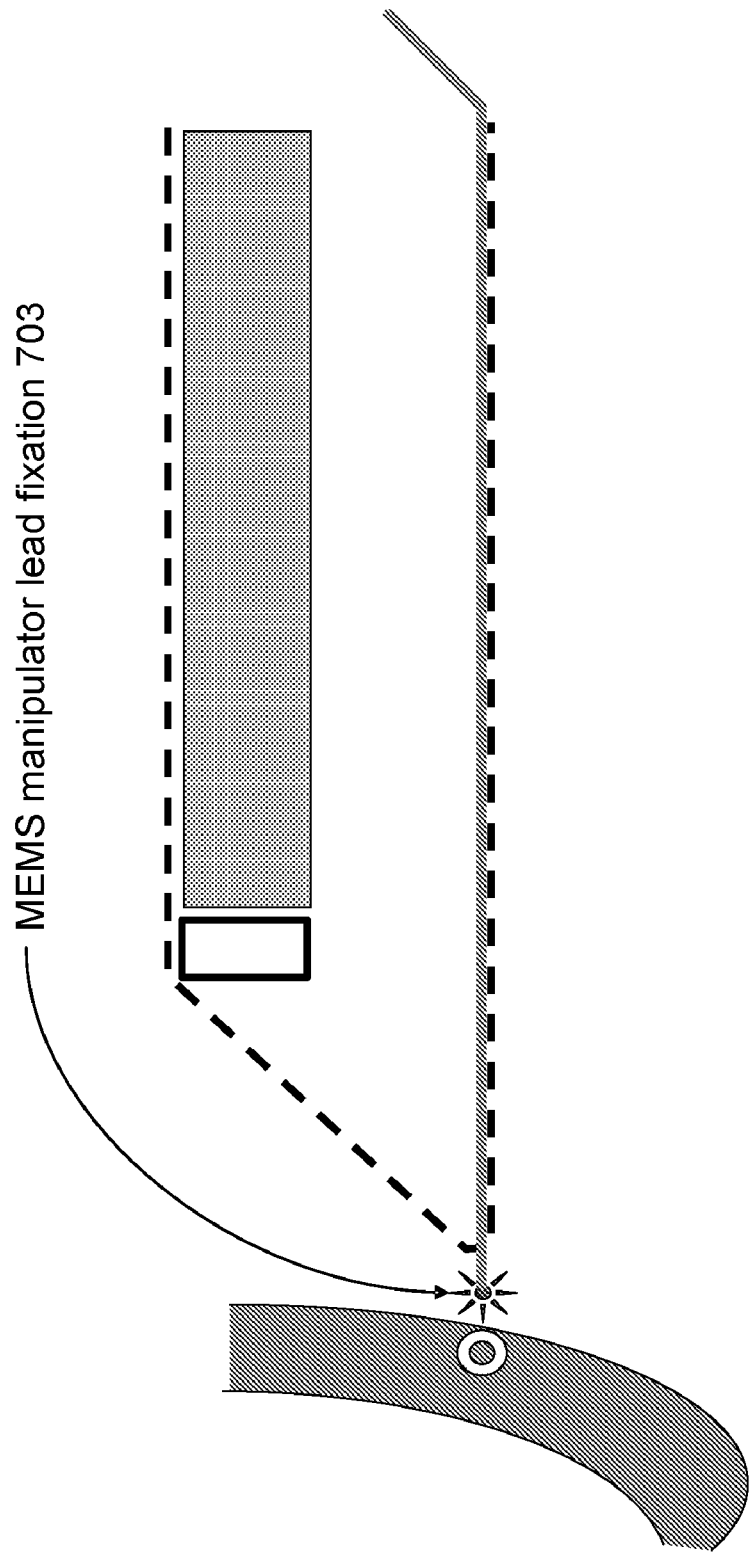

Biopsy instrument

En face view open

Side ridges 802

En face view closed

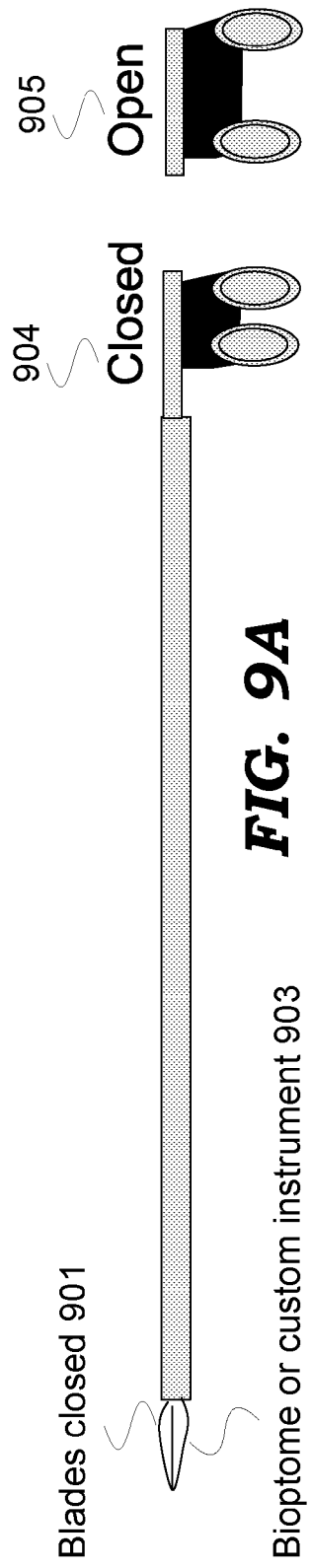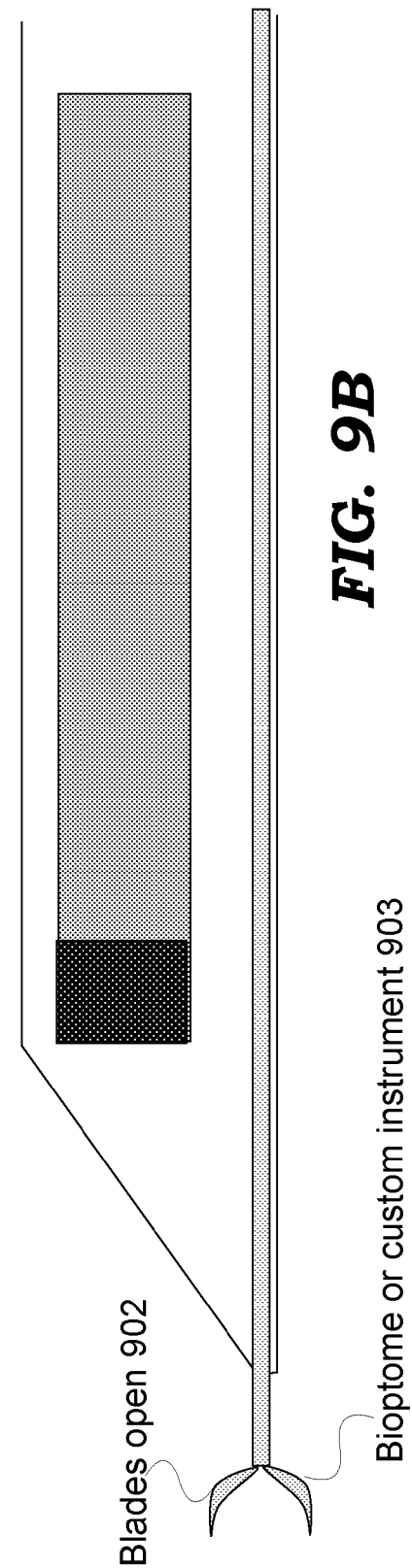

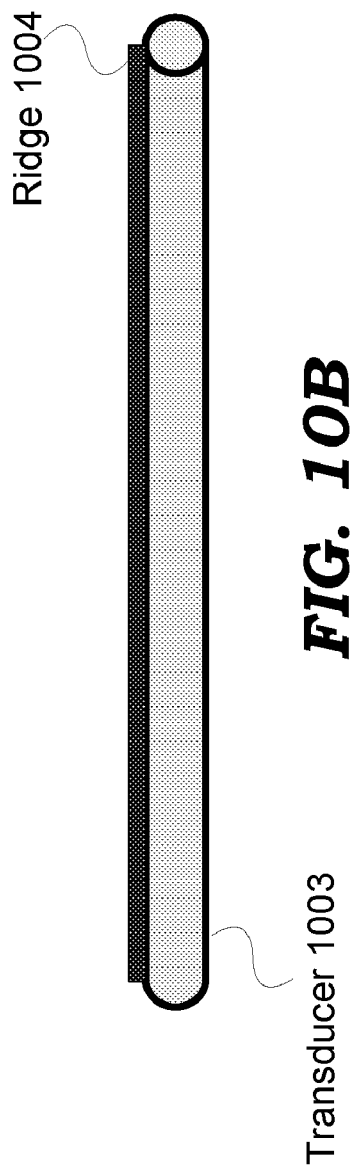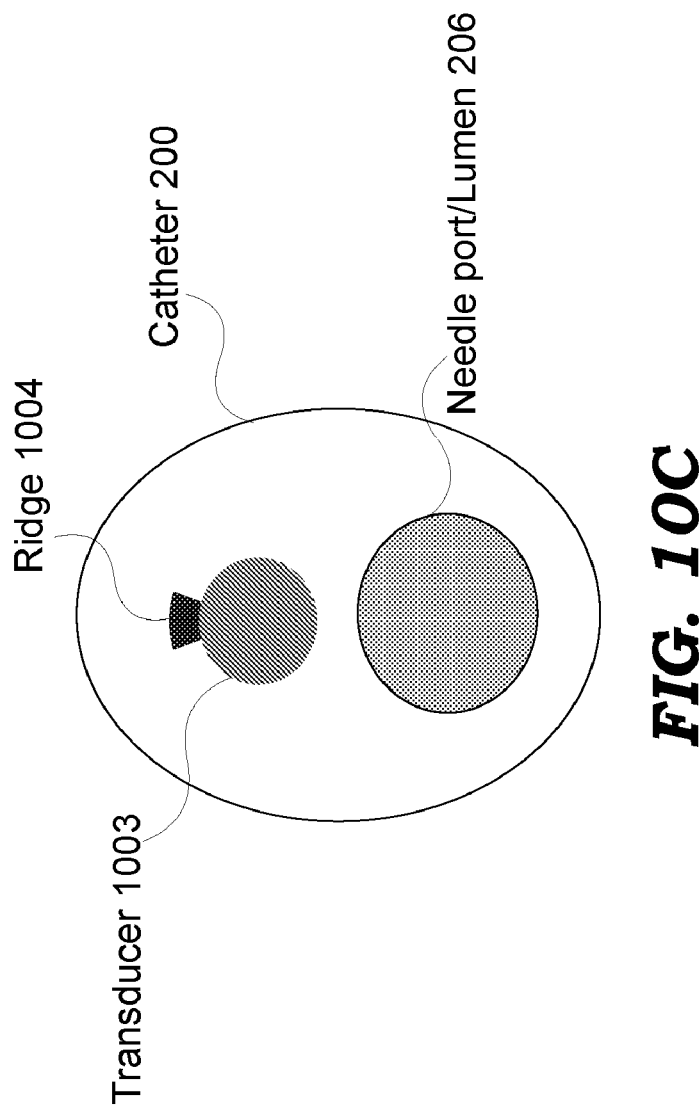
FIG. 10B
FIG. 10C

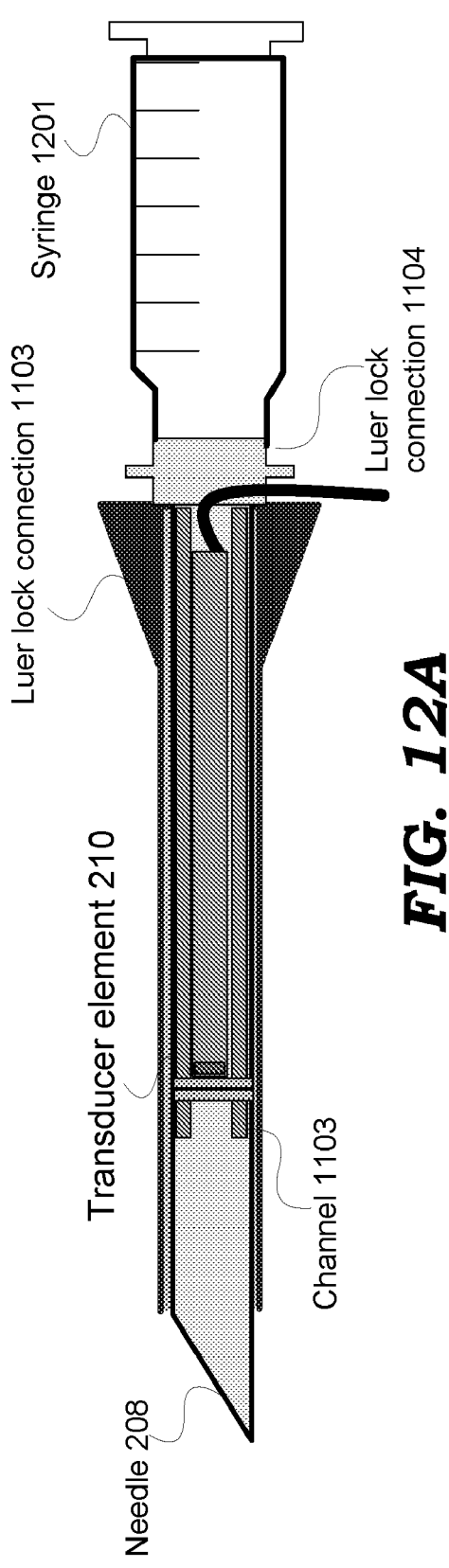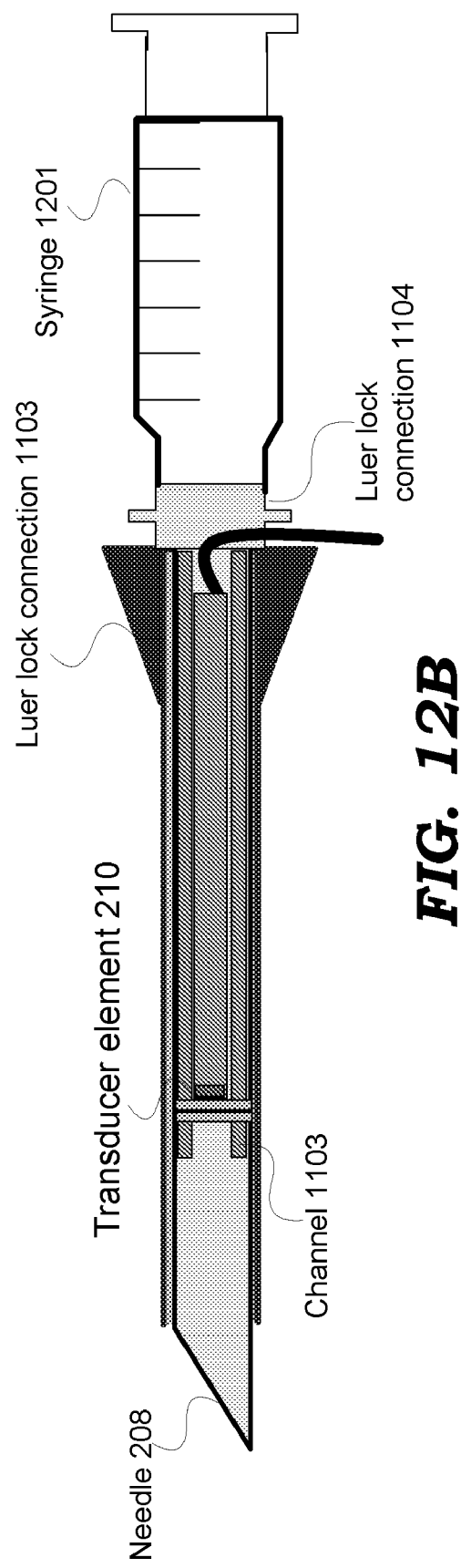

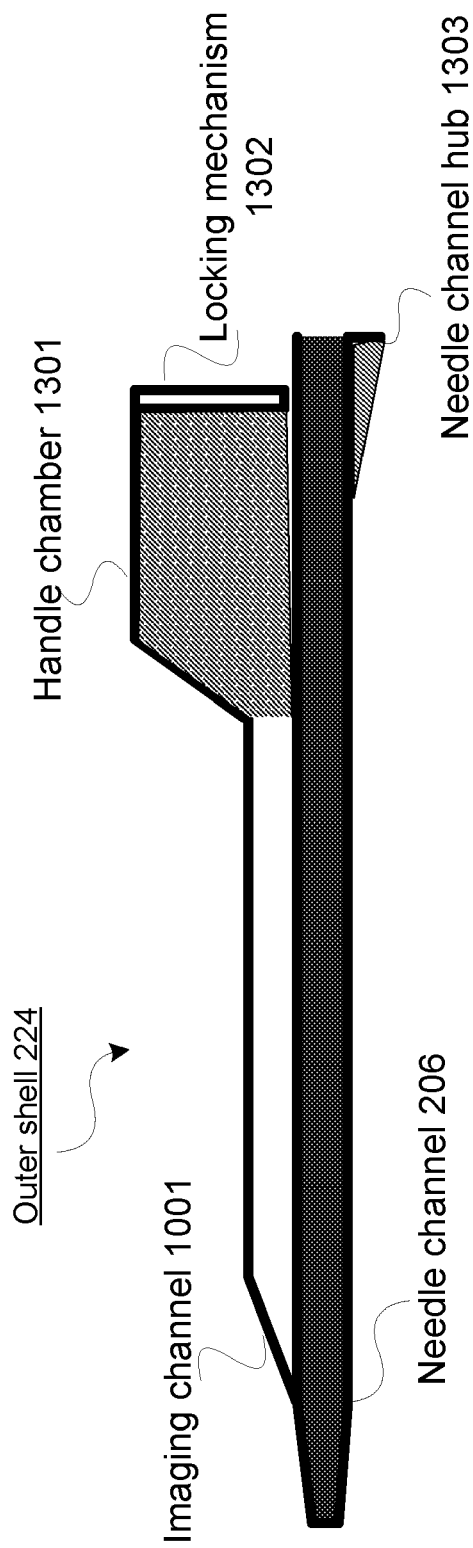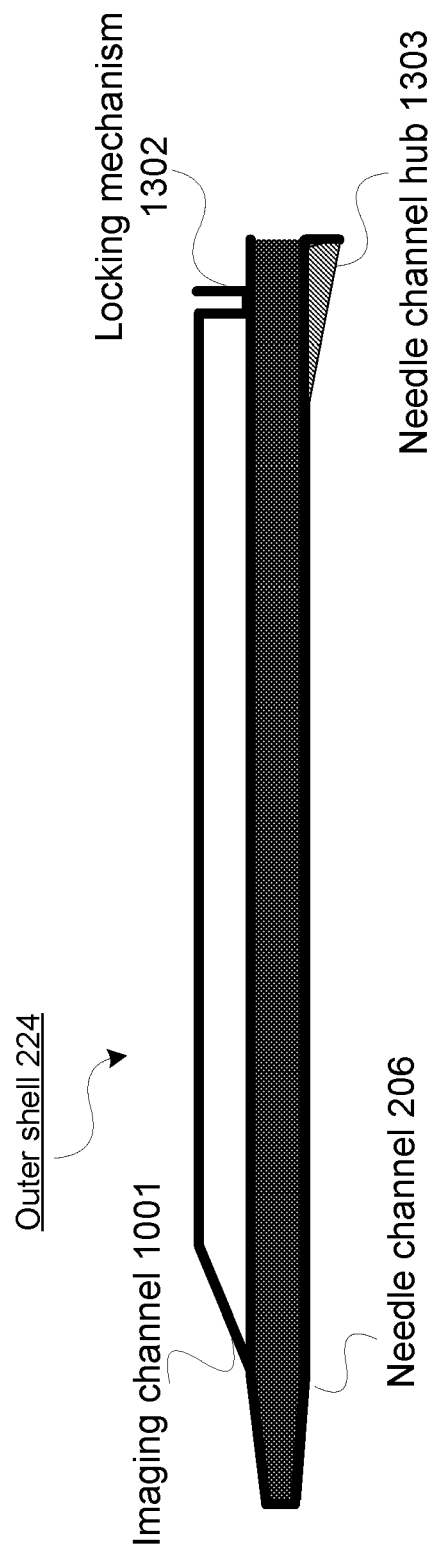
FIG. 13A
FIG. 13B

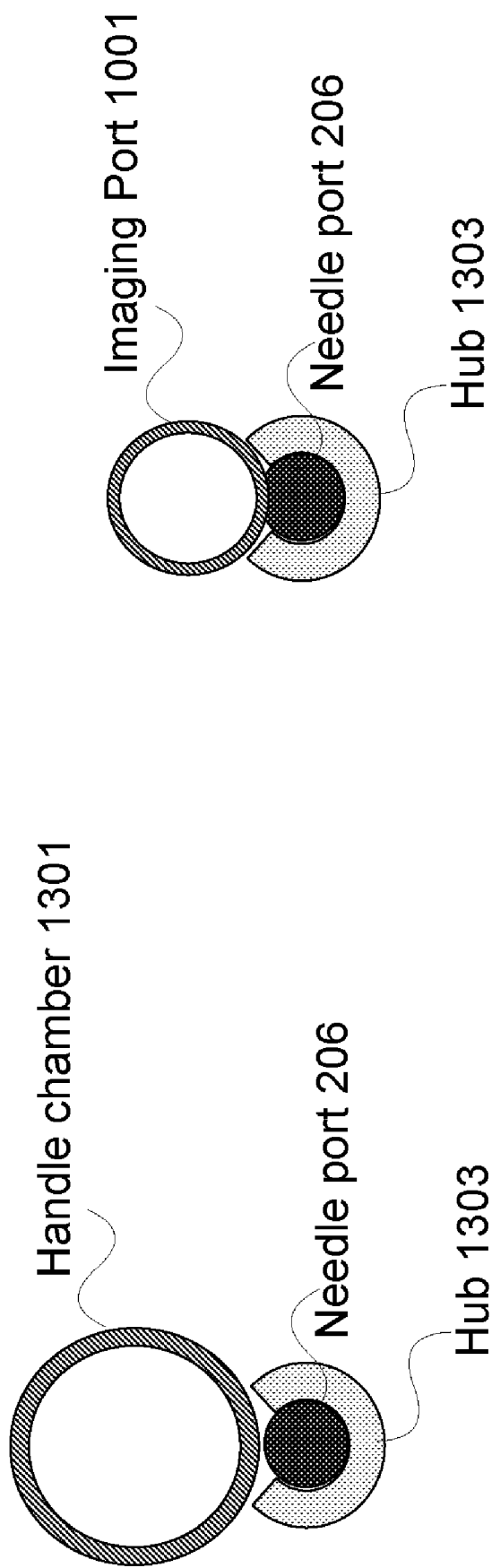

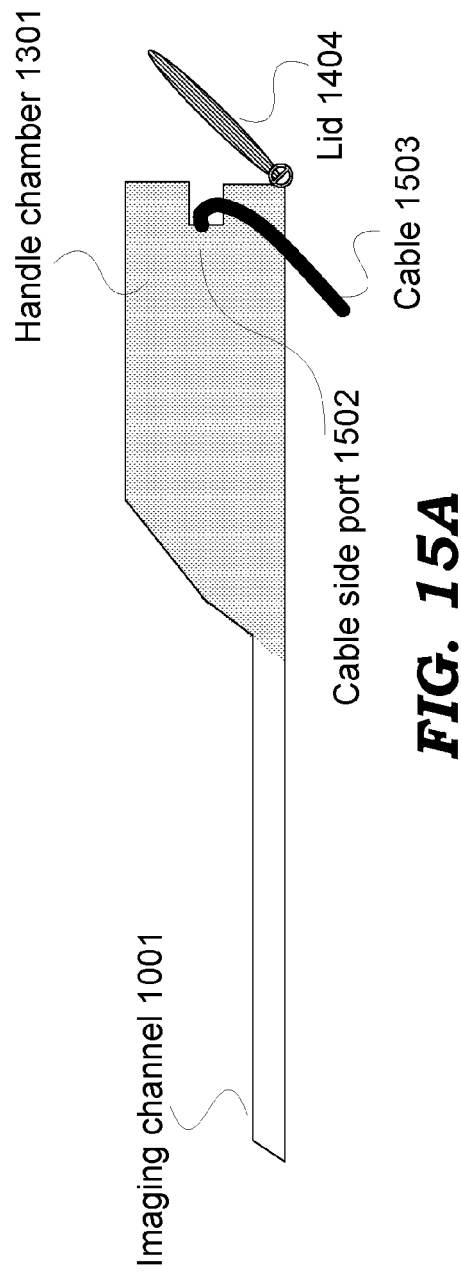
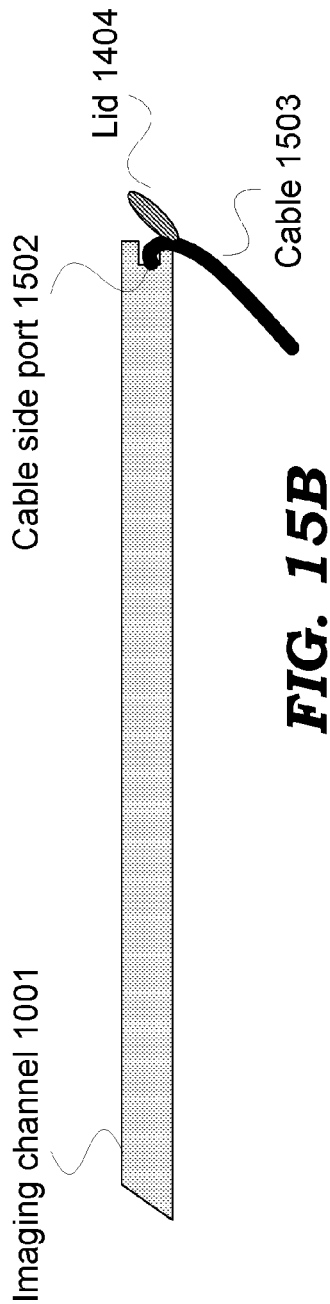
FIG. 15A
FIG. 15B
Imaging channel with locking mechanism and cable port

IMAGE GUIDED CATHETERS AND METHODS OF USE

CROSS-REFERENCE

This application claims priority to provisional U.S. Application Ser. No. 60/851,451 filed Oct. 12, 2006, the entire disclosure of which is hereby incorporated by reference into the present application.

TECHNICAL FIELD

Embodiments of the illustrated and disclosed aspects and features relate to minimally invasive interventional medical devices having integrated ultrasound imaging systems.

BACKGROUND

Ultrasound operates by creating an image from sound in three steps—producing a sound wave, receiving echoes, and interpreting those echoes to create an image.

Ultrasound has many uses in medical applications. For example, ultrasound is routinely used during pregnancy to provide images of the fetus in the womb. Generally, a water-based gel is applied to the patient's skin, and a hand-held probe, called a transducer, is placed directly on and moved over the patient. The probe typically contains a piezoelectric element that vibrates when a current is applied. In ultrasound devices, a sound wave is typically produced by creating short, strong vibrational pulses using a piezoelectric transducer. The sound wave is reflected from tissues and structures and returns an echo, which vibrates the transducer elements and turns the vibration into electrical pulses. The electrical pulses are then sent to an ultrasound scanner where they are transformed into a digital image.

While general-purpose ultrasound machines may be used for most imaging purposes, certain procedures require specialized apparatus. For example, in a pelvic ultrasound, organs of the pelvic region can be imaged using either external or internal ultrasound. In contrast, echocardiography, which is used in cardiac procedures, can require specialized machines to take into account the dynamic nature of the heart.

Ultrasound has advantages over other imaging methods such as magnetic resonance imaging (MRI) and computed tomography (CT). For example, ultrasound is a relatively inexpensive compared to those techniques. Ultrasound also is capable of imaging muscle and soft tissue very well, can delineate interfaces between solid and fluid filled spaces, and shows the structure of organs. Ultrasound renders live images and can be used to view the operation of organs in real time. Ultrasound has no known long-term side effects and generally causes little to no discomfort to a patient. Further, ultrasound equipment is widely available, flexible, and portable.

However, ultrasound does have some drawbacks. When used on obese patients, image quality is compromised as the overlying adipose tissue scatters the sound and the sound waves are required to travel greater depths, resulting in signal weakening on transmission and reflection back to the transducer. Even in non-obese patients, depth penetration is limited, thereby making it difficult to image structures located deep within the body. Further, ultrasound has trouble penetrating bone and, thus, for example, ultrasound imaging of the brain is limited. Ultrasound also does not perform well when there is gas present (as in the gastrointestinal tract and lungs). Still further, a highly skilled and experienced ultrasound operator is necessary to obtain quality images. These drawbacks do not, however, limit the usefulness of ultrasound as a medical diagnostic and treatment tool.

The use of ultrasonic apparatus for imaging areas of the human body, either alone or in combination with other instruments, is known, for example, for guiding therapeutic instruments through a catheter to a field of view within a human body. For example, ultrasound devices have been combined with catheters for insertion into a body, usually through a vein or artery, to reach a part of the human body for examination or treatment. Such devices are commonly known in the art as "imaging catheters."

For example, U.S. Pat. No. 5,704,361 to Seward et al. discloses a volumetric image ultrasound transducer underfluid catheter system. For example, FIGS. 2-9 and 11-12 of Seward et al. and their attendant description suggest specific methods of intervention for imaging purposes in the vicinity of a human heart. To reach such an area of interest within a human body, an ultrasound imaging and hemodynamic catheter may be advanced via the superior vena cava to a tricuspid valve annulus. A distal end of a cylindrical body includes a guide wire access port and a guide wire provides a means of assuring that the catheter reaches a target for imaging. A surgical tool may be fed through the catheter to the area imaged.

U.S. Pat. No. 6,572,551 to Smith et al. provides another example of an imaging catheter. Tools such as a suction device, guide wire, or an ablation electrode, may be incorporated in an exemplary catheter according to Smith et al.

U.S. Pat. No. 5,967,984 to Chu et al. describes an ultrasound imaging catheter with a cutting element which may be an electrode wire or a laser fiber. FIGS. 1 and 2 of Chu et al. also describe a balloon 14 and a means to inflate the balloon. The balloon, for example, may be utilized to dilate a vessel having strictures imaged via the imaging catheter.

Other imaging catheters are known. For example, U.S. Pat. No. 6,162,179 to Moore teaches bending (using a pull wire) an acoustic window into a known and repeatable arc for improved three dimensional imaging. U.S. Pat. No. 6,306,097 to Park et al. discloses an intravascular ultrasound imaging catheter whereby a first lumen provides access for an ultrasound imaging catheter and a second lumen provides a working port for a tool. U.S. Pat. No. 5,505,088 to Chandraratna et al. teaches using a 200 MHz transducer in an ultrasonic microscope combined with a catheter as a delivery means for the microscope to provide imaging of myocardial tissue. According to Chandraratna et al., lower frequency ultrasound transducers can provide deeper penetration in the tissue but do not provide the image quality provided by higher frequencies.

All the above-cited references are incorporated by reference as to any description which may be deemed essential to an understanding of illustrated and discussed aspects and embodiments of devices and methods herein.

SUMMARY

This summary is intended to introduce, in simplified form, a selection of concepts that are further described in the Detailed Description. This summary is not intended to identify key or essential features of the claimed subject matter, nor is it intended to be used as an aid in determining the scope of the claimed subject matter.

A device in accordance with one or more aspects described herein can include ultrasound imaging, optical imaging through the use of fiber optics, or a combination of both, to provide a wide range of imaging capabilities coupled with one or more diagnostic, therapeutic, or interventional capabilities. In one or more embodiments according to aspects herein, an interventional ultrasound device may include an elongate body having a proximal end and a distal end, one or more lumen extending through the elongate body, one or more ultrasound transducers embedded in the elongate body near the distal end, and one or more other imaging channels such as a fiber optic channel.

Illustrative aspects described herein include a minimally invasive interventional medical device that can provide ultrasound imaging coupled together with one or more interventional capabilities. The frequencies present in a sound wave output by such a device can range between 20 KHz and 300 MHz. Frequencies in the lower range, for example, below 1 MHz, and particularly in the 100-200 KHz range, can be used, for example, to provide heat therapy or to treat conditions such as blood clots. Frequencies above 1 MHz can be used to provide imaging. For example, frequencies in the 25-30 MHz range can be used to image organs such as the eye or can be used to provide imaging of small animals. Higher frequencies, for example, frequencies in the 100-200 MHz range, can be used to provide higher-resolution imaging, sometimes known as high-frequency ultrasound microscopy.

An embodiment of a device in accordance with one or more aspects and features described herein can include an ultrasonic imaging catheter having one or more forward-directed transducers that can be integrated directly into a distal end of an elongate body so as to provide a direct forward view of the tissue being accessed. Another embodiment of a device in accordance with one or more aspects and features described herein can include a minimally invasive device comprising an ultrasonic imaging catheter having an introducer needle and one or more forward-directed transducers integrated into a single elongate body so that the needle and the imaging catheter can be introduced into a body substantially simultaneously so that the needle and the path taken by the needle can be viewed as it travels through the body. An alternative embodiment of a device in accordance with aspects described herein can have one or more ultrasonic transducers located along one or more sides of the elongate body, either with or without a forward-directed transducer.

The ultrasound features of the device can serve to guide and facilitate surgical procedures performed with the device. For example, a medical professional such as a surgeon can receive direct vision of a targeted area in real time.

A wide variety of other interventional elements also can be incorporated into such a device.

For example, in some embodiments of a device in accordance with one or more aspects and features described herein, an ultrasound imaging transducer can be combined with an interventional catheter having an introducer needle so that the catheter can be inserted under ultrasound imaging guidance directly into the target site. For example, the catheter can be inserted directly through the chest wall into the heart without having to make entry through another means such as through a blood vessel in a human leg. Once at the target location, the needle can be removed and replaced with another instrument such as a biopsy needle or the entire assembly can be removed after a guide wire is introduced so that other instruments can be delivered to the target site.

In another embodiment in accordance with one or more aspects herein, a medical device is provided that can comprise one or more ultrasound transducers coupled or associated with a syringe element for delivery or withdrawal of fluids at a treatment site. An exemplary syringe that can be used is a needle assembly such as is described in U.S. Pat. No. 6,592,559 to Pakter et al., which can deliver multiple needles to multiple sites within the body.

According to other aspects, at the proximal end of such a device, an anchoring portion is provided for anchoring the device to a human body once the device is image-guided to the diagnosis or treatment site.

According to aspects herein, the elongate body of such a device may be formed from one or more of a variety of materials such as silicone, Teflon, polyurethane, PVC, and/or elastomeric hydrogel. According to some aspects, the elongate body may be cylindrical in shape and may include, for example, a catheter or vascular sheath.

These and other aspects will be discussed with reference to the drawings, a brief description of which follows.

BRIEF DESCRIPTION OF THE DRAWINGS

The above-described aspects and embodiments of devices and procedures and other features and advantages can be appreciated and understood by reference to the following detailed description when considered in connection with the accompanying drawings wherein:

FIG. 1A provides a side view of a device in accordance with aspects described herein, and also includes six cross-sectional views along the length of the depicted embodiment. FIG. 1B provides a cross-sectional view of a device according to the embodiment illustrated in FIG. 1A. FIG. 1C provides further detail of the distal end of the device of FIG. 1A. FIG. 1D provides a further view of a minimally invasive device having a forward-directed ultrasonic transducer and an introducer needle.

FIG. 2A shows the device of FIG. 1 without a needle housed within the device lumen. FIGS. 2B-2E show side and cross-sectional views of embodiments of devices having various types of distal ends and apertures for multiple lumens in accordance with one or more aspects described herein.

FIGS. 4A and 4B show side and cross-sectional views of a device having multiple lumens in accordance with one or more aspects described herein.

FIGS. 5A-5E show views of an ultrasound transducer for use in a minimally invasive interventional device in accordance with one or more aspects described herein. FIG. 5A depicts one embodiment of a forward-projecting small ultrasound transducer according to one or more aspects described herein. FIG. 5B depicts arrangements of transducer elements that can be made in different housing configurations. FIGS. 5C and 5D depict design options for a flat-faced and a round-faced housing, respectively, for a forward-projecting ultrasound transducer for use in a device in accordance with aspects described herein.

FIGS. 7A and 7B depict embodiments of a device having a MEMS position manipulator in accordance with one or more aspects described herein.

FIGS. 9A and 9B show views of a retrieval instrument that can be used in a minimally invasive device in accordance with one or more aspects described herein.

FIGS. 10A-10C depict aspects of an imaging catheter in accordance with one or more aspects herein wherein an ultrasound transducer housing can be configured to be interchangeable with an outer sheath. FIG. 10A depicts aspects of a hollow outer catheter having a port configured to house an imaging device such as an ultrasound transducer. FIG. 10B depicts an embodiment of an ultrasound transducer having a ridge along its length so that it may be inserted into a housing such as is shown in FIG. 10A. FIG. 10C depicts a cross-sectional view of an exemplary catheter body having a channel into which an ultrasound transducer with a ridge as shown in FIG. 10B is inserted.

FIGS. 12A-12F depict aspects of an imaging catheter having a single channel for both a needle and an ultrasound transducer. FIGS. 12A and 12B depict such an imaging catheter in combination with a syringe element at a proximal end. FIG. 12C depicts aspects of such a catheter wherein a guide wire can be inserted to permit an additional device to be directed to a target site. FIG. 12D depicts an embodiment of a device in accordance with aspects herein wherein a guide wire is passed through a sheath. FIGS. 12E and 12F depict aspects wherein the transducer and needle are removed from the single channel to permit use of a syringe, for example, to deliver or remove fluids from the target site.

FIGS. 13A-13D embodiments of an outer shell for use with an imaging catheter in accordance with one or more aspects described herein. FIG. 13A depicts an embodiment of an outer shell for use with a transducer having a handle portion in accordance with aspects herein. FIG. 13B depicts an embodiment of an outer shell for use with a transducer without a handle portion in accordance with aspects herein.

FIGS. 15A and 15B depict embodiments of a portion of an outer shell having a locking mechanism in accordance with one or more aspects described herein.

DETAILED DESCRIPTION

Figure 1A:
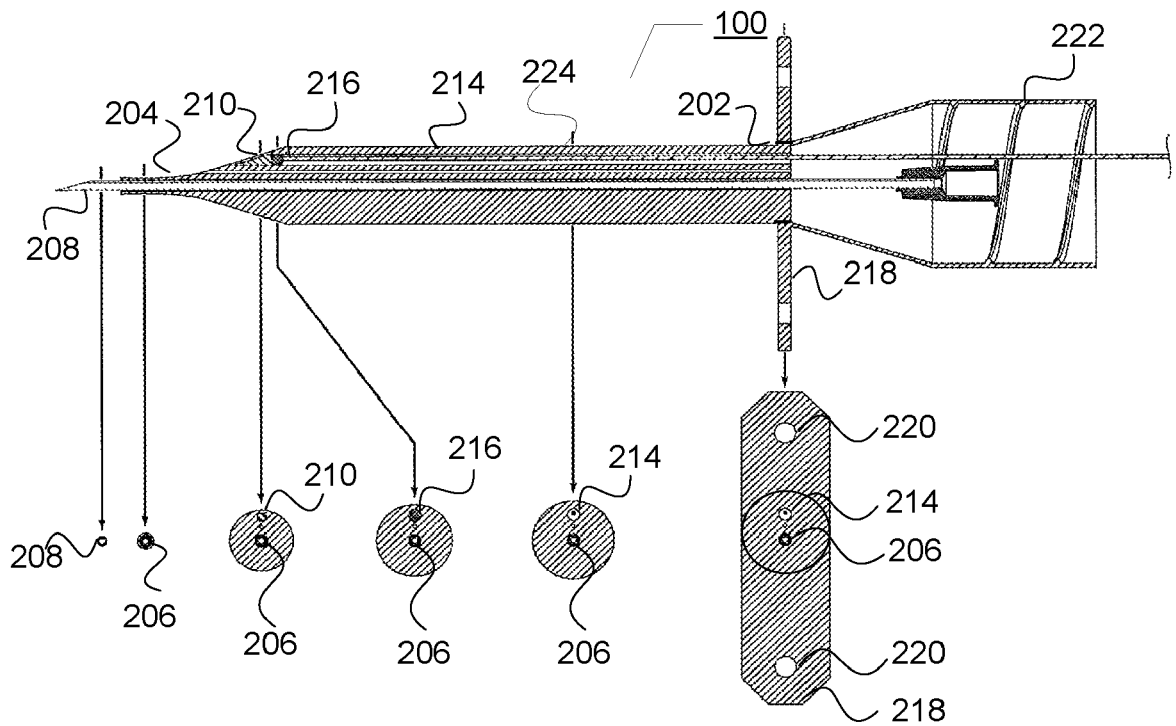
FIGS. 1A-1D present views of one embodiment of a minimally invasive device in accordance with aspects described herein.

The aspects summarized above can be embodied in various forms. The following description shows, by way of illustration, combinations and configurations in which the aspects can be practiced. It is understood that the described aspects and/or embodiments are merely examples. It is also understood that other aspects and/or embodiments can be utilized, and that structural and functional modifications can be made, without departing from the scope of the present disclosure.

Minimally invasive procedures provide physicians with access to internal organs and structures via a small number of incisions in the patient's body. Minimally invasive procedures are generally preferable over open procedures because they require only small incisions, thus reducing trauma to the body, lessening recovery time, and reducing costs. The medical instruments used in performing such procedures are generally similar to those used in open surgical procedures except they include an extension such as a tubular extension between the end of the instrument entering the surgical field (i.e., the operable end of the tool, instrument or device) and the portion gripped by the surgeon.

Typically, minimally invasive procedures involve up to five incisions up to one inch in length. The treatment area is then accessed by inserting one or more cannulas or sleeves through the incisions to provide entry ports through which instruments are passed. Alternatively, access to the treatment area can sometimes be obtained using a natural bodily opening such as the throat or rectum. In procedures using this approach, a cannula or sleeve is inserted into the bodily opening and surgical instruments are passed to the treatment site, either through the cannula/sleeve or directly through the bodily opening.

While minimally invasive procedures provide numerous advantages over open procedures, they generally do not provide a physician with a direct view of the targeted sites. Further, many parts of the anatomy are rather complex and/or small and thus require particular precision and delicate handling. It is therefore desirable to provide precise imaging techniques for use during minimally invasive procedures.

In general, the illustrated embodiments and aspects provide a device that couples an imaging system and a delivery system and/or minimally invasive interventional device. The delivery system can include, for example, delivery of materials to or from a target site or delivery of instruments and devices to a target site.

In accordance with aspects described herein, an ultrasound imaging catheter can comprise one or more small ultrasound transducers integrated into an elongate body, either as forward-directed transducers for direct, head-on imaging or combined with one or more side-directed transducers which can provide additional imaging or other ultrasound applications to the patient. In addition, such ultrasound imaging can also be combined with optical imaging through the use of one or more fiber optic bundles disposed though the elongate body.

An imaging system in accordance with aspects and features described herein can guide and facilitate many different procedures, thereby significantly assisting in the access of and performance of procedures on organs, structures and cavities within the body, particularly during minimally invasive procedures. The described devices and methods are compatible with all surgical and diagnostic devices and will allow bedside emergency procedures. Ultrasound provides particular benefits because it is biologically safe and uses non-radiating energy to provide detailed anatomic and, in some cases, functional images. The images generated by devices described herein can provide a user with direct vision within the body in real time. Further, ultrasound provides a user with visualization of structures as well as within and beyond structures.

In certain embodiments, the device can comprise an ultrasound imaging catheter that incorporates one or more variable frequency ultrasound transducers operating at one or more frequencies within the frequency range of from 20 KHZ to 200 MHz. The various frequencies of the ultrasound transducer can be used for different purposes and provide different beneficial results. Frequencies in the lower range, for example, below 1 MHz, and particularly in the 100-200 KHz range, can be used, for example, to provide heat therapy or to treat conditions such as blood clots. Frequencies above 1 MHz can be used to provide imaging. For example, frequencies in the 25-30 MHz range can be used to image organs such as the eye or can be used to provide imaging of small animals.

Higher frequencies, for example, frequencies in the 100-200 MHz range, can be used to provide higher-resolution imaging, sometimes known as high-frequency ultrasound microscopy.

Devices and methods such as are described herein are suitable for use in a variety of medical procedures. In certain embodiments, the device can comprise conventional catheters including, for example, biopsy catheters, ablation catheters, and mapping catheters, in combination with the novel imaging aspects described herein. In other embodiments, the device can comprise one or more interventional devices (e.g. syringe, forceps, biopsy instruments, clamps, retractors, etc.) that may be compatible with a catheter such as a biopsy catheter, ablation catheter, mapping catheter, or other form of sheath. In some embodiments, the device can also be compatible with instrument such as videoscopes and delivery needles such as those used for stem cell therapy. In still other embodiments, the devices can be compatible with fiber optics such as those used for vision therapy.

The devices and methods of various embodiments of an imaging catheter such as those illustrated in FIGS. 1-17 and described herein can be used in various minimally invasive surgical procedures and in other diagnostic and therapeutic applications. One skilled in the art will appreciate that the aspects and embodiments of an imaging catheter as described herein, although advantageously suited for such procedures on humans, can have other uses, such as for veterinary procedures and open medical techniques as well as minimally invasive procedures in humans. Further, while the devices of the present invention are described with particular reference to catheters, this shall not be construed as limiting the devices to the these embodiments, as it is contemplated and thus within the scope of the illustrated devices to adapt the devices described herein so as to be in the form of any type of minimally invasive device (e.g. syringes, sheaths, wires, forceps, biopsy instruments, clamps, retractors, etc.).

Further, while certain devices, systems and methods are described herein with particular reference to pericardial access devices, systems, and methods, this shall not be construed as limiting, as it is contemplated to adapt the devices, systems and methods described herein so as to be used in any of a number of procedures, including, but not limited to: various cardiovascular procedures; general micro-surgery; biopsy, drug and device delivery; vascular procedures; urology; thoracic procedures; otorhinolaryngology (ear, nose and throat); orthopedic procedures; neurosurgery; gynecologic procedures; gastroenterologic and general procedures; colon and rectal procedures; pericardiocentesis; thoracentesis; ascites tap; ventricular lead placements; and electrical and electromechanical mapping of the heart. As such, it is contemplated that the specific design parameters, other characteristics set forth hereinafter, and methods in relation thereto can be modified to provide appropriate dimensions and geometries as required to perform such other techniques. For example, the length and diameter of the device as herein described is adapted to suit the particular conditions for a given procedure. Thus, the disclosure to follow should is illustrative only and should not be construed as limiting in any configuration of a device as described herein.

Referring now to the various figures of the drawing wherein like reference characters refer to like parts, FIGS. 1-4, 6, 10-12, 13, and 16 depict various views of embodiments of a minimally invasive device 100 according to one or more aspects described herein. Devices for performing minimally invasive procedures, including sheaths (e.g., vascular sheaths), catheters, and interventional devices (e.g. forceps, biopsy instruments, clamps, retractors, etc.) are conventional in various forms as described above and, thus, although described and shown with reference to preferred embodiments, the general features (e.g. size, shape, materials) of the a device 100 may be in accordance with conventional devices.

FIG. 1A depicts a side view of a device 100 in accordance with one or more aspects and features described herein. Device 100 can be used to provide a three-dimensional mapping system solely using an incorporated ultrasound system or in connection with other imaging modalities such as computed tomography, magnetic resonance, videoscopy. When the device is in the form of a catheter or sheath, this will allow stereotactic and remote/robotic operation of devices inserted and manipulated through device 100. In such a system, an imaging modality (ultrasound, CT or MRI) can be used to generate a three-dimensional image. The device can interactively use the generated images to be directed either manually or through an automated or semi-automated process for deployment to a target area displayed in the three-dimensional image. Device 100 can be used in connection with an ultrasound display system (B mode image or 3D image) that interfaces with the device to produce and display the images.

Figure 16A:
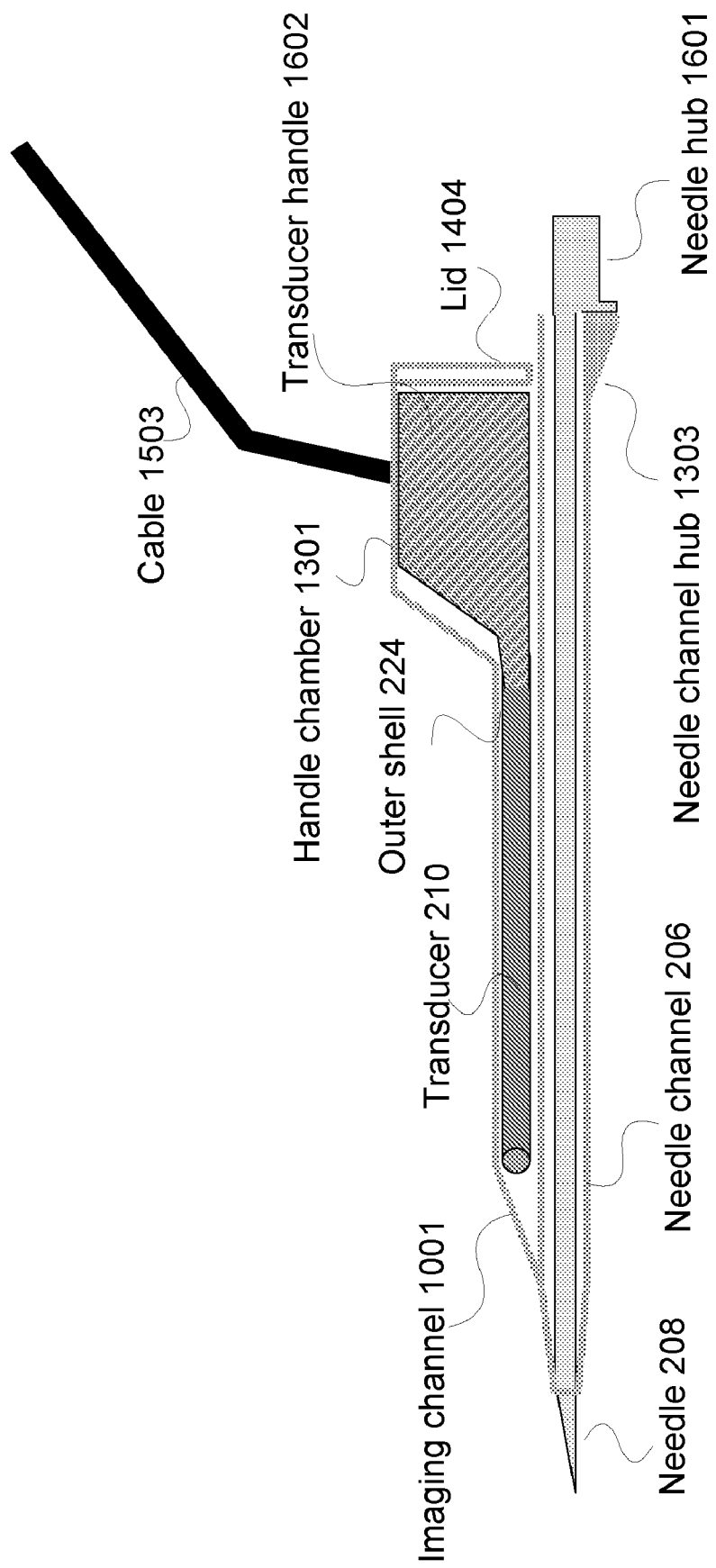
FIGS. 16A and 16B depict embodiments of an imaging catheter having an introducer needle integrated into a single device with an ultrasound transducer in accordance with one or more aspects described herein.
Figure 16B:
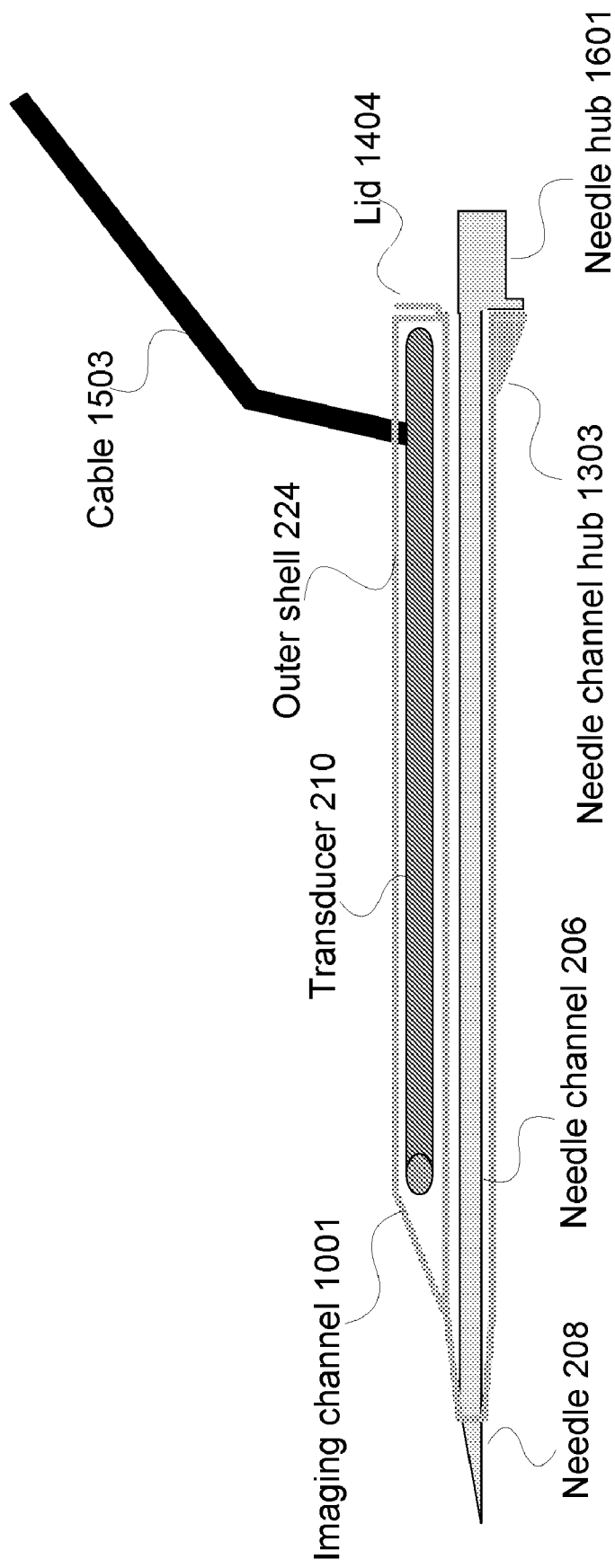

In an embodiment of a device described herein, as shown in FIG. 1A, and also as shown in FIGS. 16A and 16B, device 100 can be in the form of a catheter and comprises an elongate body 200 having an outer shell 224 and a proximal end 202 and a distal end 204. In accordance with conventional practice, the term "proximal end" is used herein to describe the specified end closest to the medical personnel manipulating the device, and the term "distal end" is used to describe the opposite end of the device that is placed near or within a patient). The elongate body 200 can be fabricated of any conventional materials used in forming catheters, sheaths, and interventional devices. For example, when in the form of a catheter, the outer shell 224 of elongate body 200, for example, as shown in FIGS. 13A and 13B, can be fabricated of, for example, silicone, Teflon, polyurethane, PVC, and elastomeric hydrogel (AQUAVENE). In certain embodiments, the elongate body 200 can be cylindrical in shape; in other embodiments, elongate body 200 can be a squared cylinder, oval cylinder or other shape as may be appropriate for a particular application or use.

The dimensions of the elongate body 200 are not particularly limited and can vary depending on the ultimate use of device 100, the insertion point, and the distance to the target area from the insertion point. The diameter of the elongate body 200 can be affected by the size of an anatomical structure in which it is to be inserted. For example, elongate body 200 can be longer and more slender for deep abdominal structures such as the kidneys or pelvic structures such as the ovaries or uterus, or can be shorter and wider for delivery of devices into more shallow structures such as a joint, muscle, the liver, or the heart. The diameter of the elongate body 200 can also be affected by the desired size of the incision through which device 100 is inserted and which must subsequently be closed or by the purpose for which it is used. For example, the diameter of the elongate body 200 can be smaller for aspiration of fluids from a target site or larger if additional ports or device delivery are desired.

For example, when device 100 is in the form of a vascular sheath, the outer diameter can vary depending on the targeted blood vessel through which the elongate body 200 is inserted. In an embodiment, device 100 can be in the form of vascular sheaths used during cardiac procedures and can be inserted through a blood vessel in the upper thigh or, alternatively, can be inserted through a blood vessel in the arm. In another embodiment, device 100 can be inserted by anesthetizing an area the patient's upper thigh and inserting the elongate body 200 through a blood vessel in the upper thigh and towards the heart. In this embodiment, the elongate body 200 can have a length sufficient to traverse this pathway. In an additional embodiment, device 100 can have an introducer needle 208 integrated therein, which can enable device 100 to penetrate directly into the chest wall of a patient for direct access to the heart without the need for access through the vascular system.

Device 100 can also be in the form of a sheath used during a laparoscopic procedure, and in such a case, the elongate body 200 can generally have an outer diameter in accordance with conventional laparoscopic sheaths and will have a length that provides access to the target site.

Further, the device can be used as a minimally invasive conduit from the skin surface to the target site to allow passages of catheters, guide wires, and instruments through elongate body 200, can the elongate body 200 can be sized to allow these various instruments to be passed therethrough.

In an exemplary embodiment described in more detail herein, device 100 can be in the form of a catheter that can be introduced through the chest to access various internal structures using minimally invasive techniques. As such, the elongate body 200 can have an outer diameter ranging from about 1 F to 15 F (wherein 1 F=0.33 mm) and a length ranging from about 1" to 20". Specific lengths and diameters can be provided based on the insertion site of the catheter, the distance to the desired target site(s), and the space required for insertion of one or more interventional devices through the elongate body 200.

In other embodiments, device 100 can be in the form of any interventional device that can be, for example, inserted through a sheath or catheter to access various internal structures using minimally invasive techniques. As such, the elongate body 200 can have an outer diameter sized so as to fit within conventional sheaths or catheters, and a length suitable to access the desired target site(s) through the sheaths or catheters.

In some embodiments, for example as shown in FIG. 1A, a Luer lock 222 can be provided at a proximal end 202 of the elongate body member 200. Luer lock 222 can be used to connect the device to, for example, a Touhey or a syringe (not shown). In some embodiments, a hemostatic valve and/or silicone pinch valve or water tight valve (not shown) can be located at the proximal end 202 of the elongate body 200 to prevent leakage of materials, such as blood and body fluids, out of device 100. In some embodiments, a side-arm (not shown) in fluid communication with one or more lumen 206 may also be located near the proximal end 202 of the elongate body 200. An aspiration device or syringe can be connected to the side arm, if desired, to aspirate blood clot and other materials through the lumen 206 or to inject water, saline, contrast agent or similar material may be injected through device 100 to a target site.

Figure 1B:
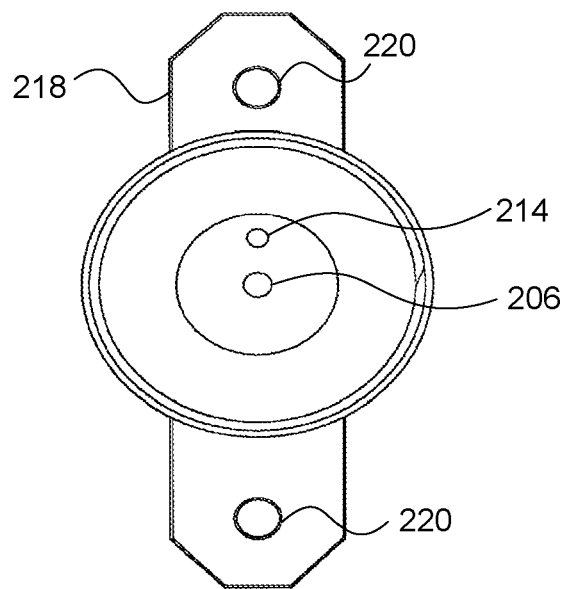

As shown in FIG. 1A and FIG. 1B, device 100 also can be provided with one or more anchoring portions 218 at the proximal end 202 of the elongate body member 200. The anchoring portion 218 can assist in maintaining device 100 in proper position during use and can prevent or inhibit unwanted motion of the device. If desired, one or more sutures (not shown) can be used with the anchoring portion 218 for suturing the device to the skin to provide additional stability of the device during use. For example, the anchoring portion 218 can be provided with one or more suture holes 220. In some embodiments, anchoring portion 218 can be slidably movable along a length of the elongate body member 200 and can lock into place, for example by locking into one of a plurality of detents (not shown) along the length of the elongate body to provide anchoring of the catheter or sheath at different depths of penetration into the body.

One or more guide wires (not shown) may further be incorporated into the elongate body 200 for steerable guidance of device 100 to the target area.

Figure 1C:
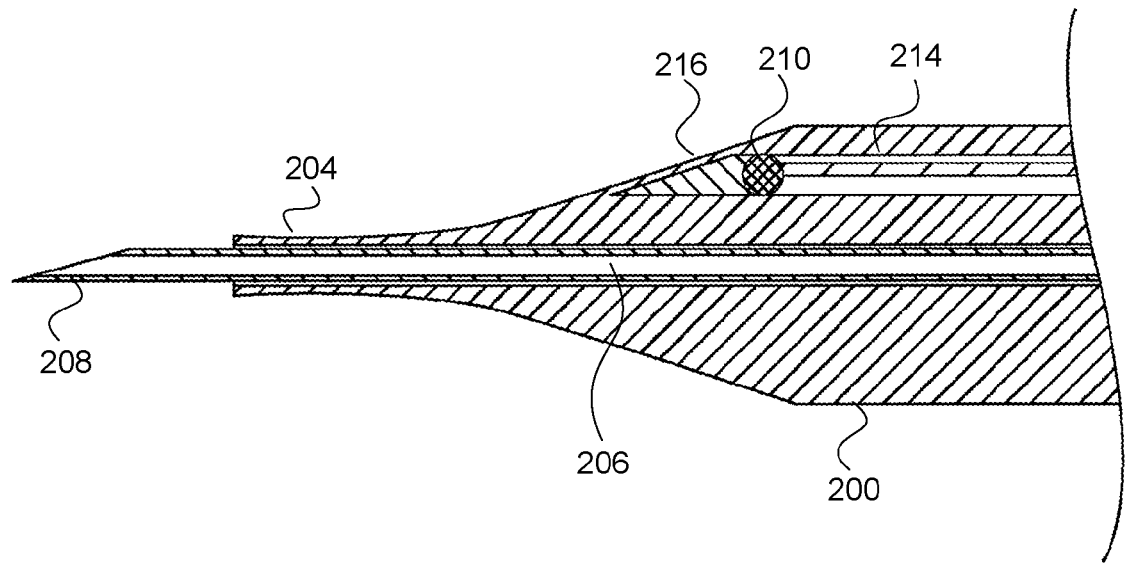
Figure 1D:
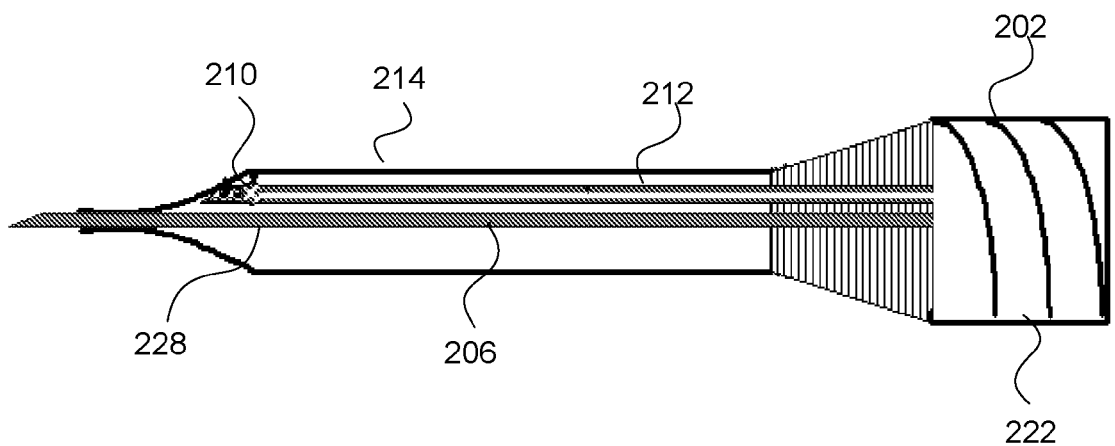

In certain embodiments, device 100 can be in the form of a catheter or sheath and the elongate body 200 is provided with one or more lumen 206 extending therethrough. See FIGS. 1A-1D and 2A-2E. Depending on the use of the lumen 206, the design and configuration can vary. For example, in some embodiments as described further herein, a central wire lumen 206a can be provided through which a needle 208 is insertable as shown in FIGS. 1A, 1C, and 1D. The needle can be used, for example, to puncture various target sites to allow direct access to the part of the body being treated and inject or withdraw materials from the target site. Central wire lumen 206a can be sized to accommodate the size of the needle 208. For example, for an 8-30 gauge needle 208, lumen 206 can be at least 8-30 gauge so as to accommodate a needle of such a size.

Figure 2A:
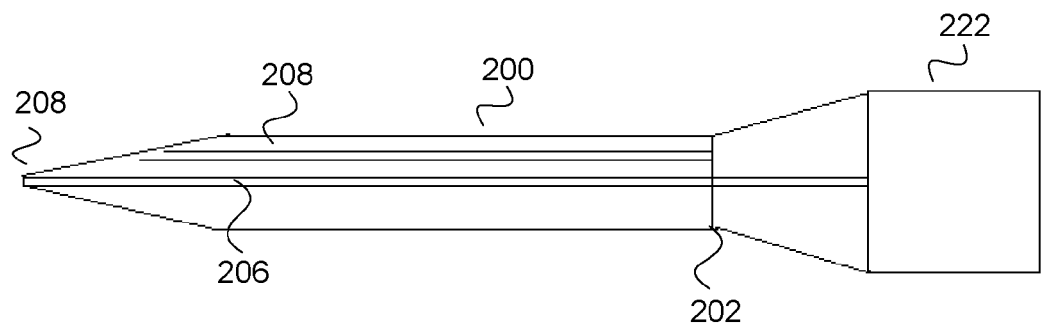
FIGS. 2A-2E show additional side views of the device of FIG. 1.
Figure 2B:
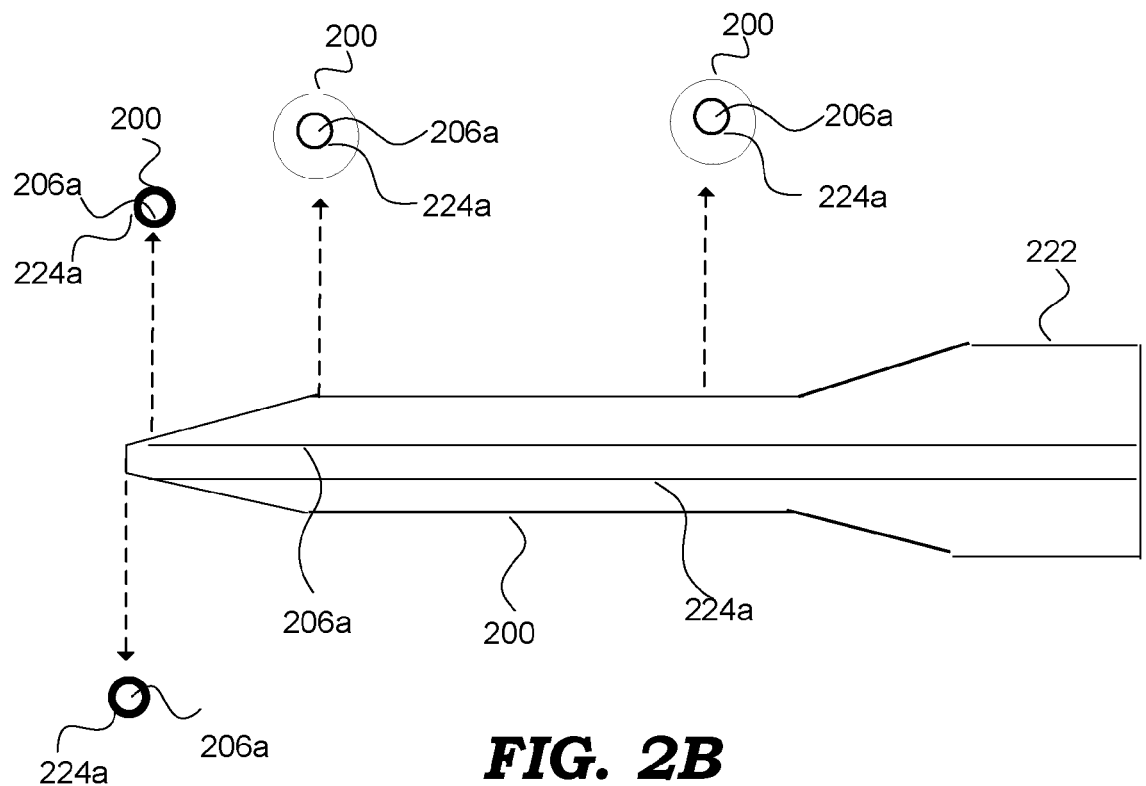
Figure 2C:
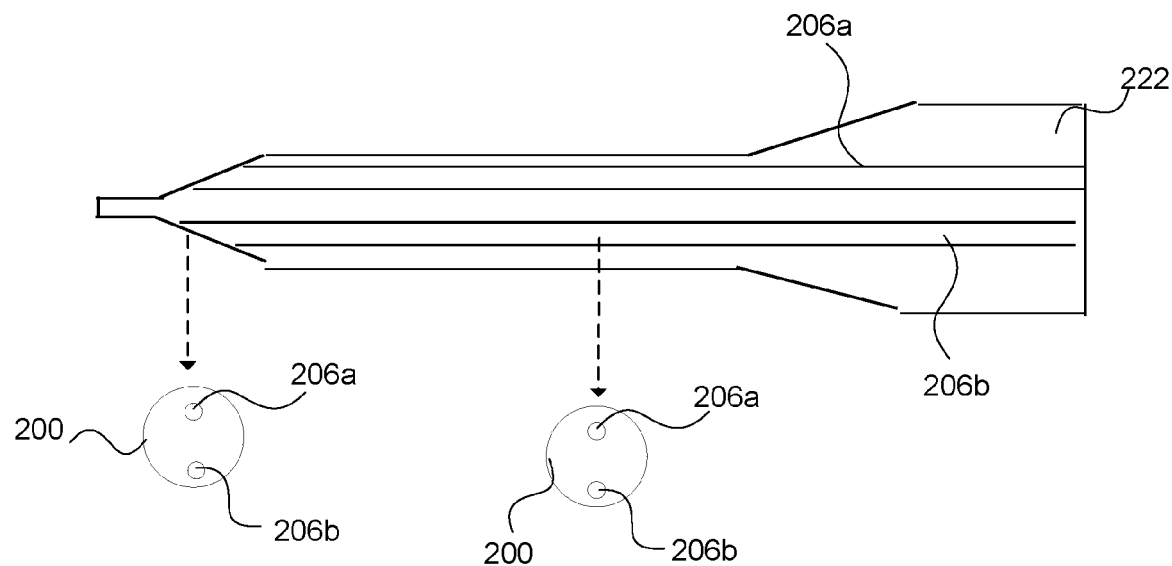
Figure 2D:
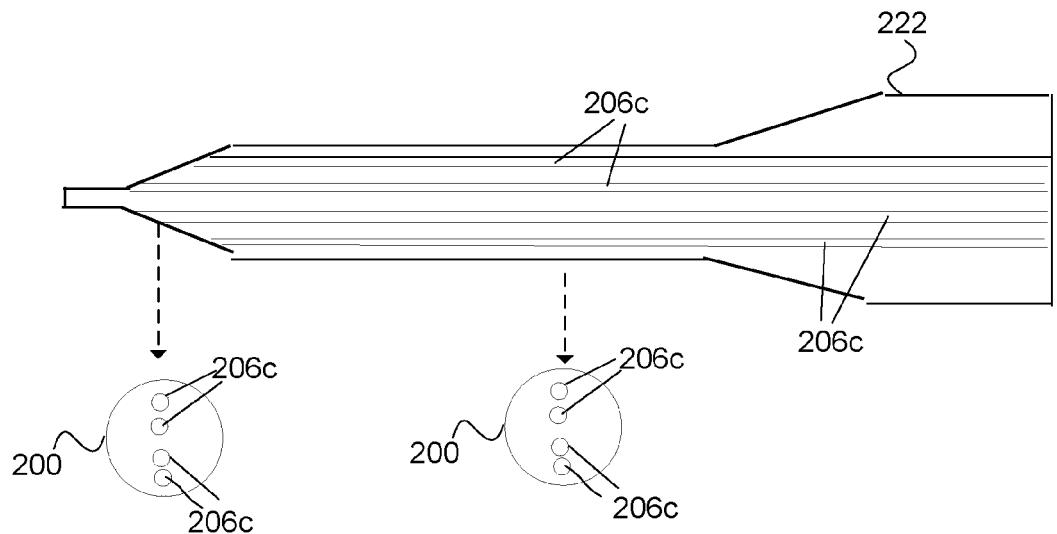

As shown in FIG. 2C, in some embodiments, device 100 can also be provided with one or more interventional device lumen 206b, either with or without the presence of a central wire lumen 206a, through which one or more interventional devices can be inserted and manipulated. It can be readily appreciated that these lumen 206b also can be sized so as to allow for insertion and manipulation of the interventional devices therethrough.

As shown in FIG. 2C, in some embodiments, device 100 is provided with one or more injection/aspiration lumen 206c through which materials can be injected and removed. For example, emboli, blood clots, and other materials can be evacuated from a blood vessel using an aspiration technique, and agents, such as medicaments, anticoagulants, and contrast media may be injected into the treatment site using, for example, a syringe in connection with the lumen 206c. As such, these lumen 206c can be sized in accordance with conventional injection/aspiration lumen 206c.

Figure 2E:
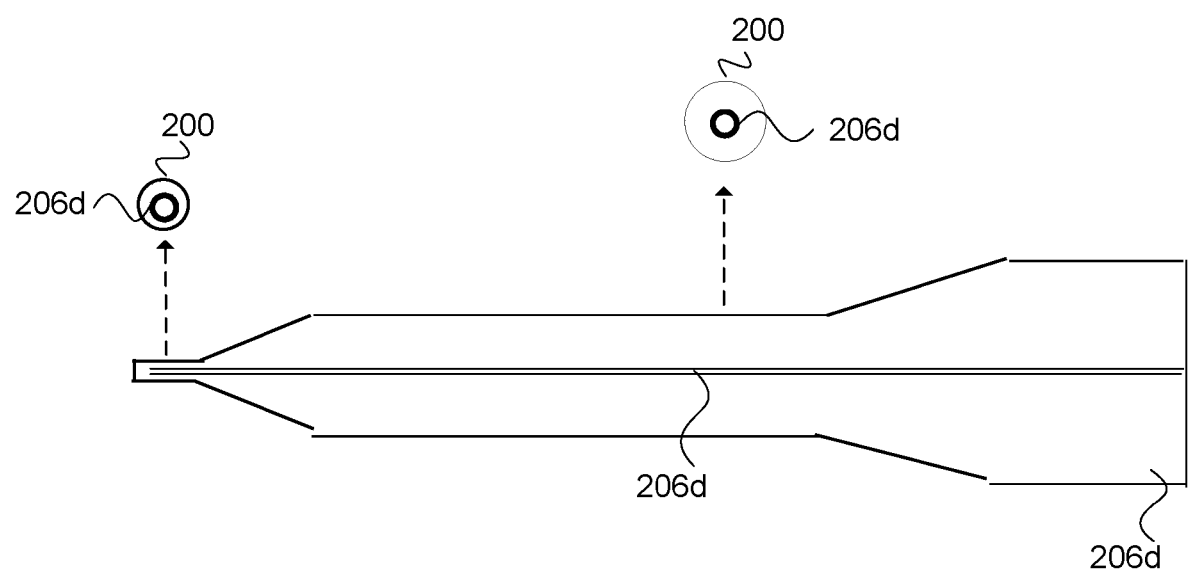

In other embodiments, for example, as shown in FIG. 2E, a guidewire lumen 206d can be provided through which a guidewire is inserted for steerable guidance of device 100 into the desired site. In a manner similar to that noted above with respect to other lumen 206, lumen 206d can be sized to accommodate conventional guidewires.

In some embodiments, such as is shown in FIGS. 2B, 2C, 2D, and 2E, device 100 can be provided with any combination of these lumen 206a, 206b, 206c, 206d. In addition, in some embodiments, lumen 206a, 206b, 206c, 206d can be used interchangeably to carry therapeutic, guidance, or other devices in device 100. For example, three lumen 206 can be provided and can be used to insert, for example, a fiber optic endoscope, a biopsy needle, and a therapy delivery needle. In other embodiments, up to five lumen 206 can be provided, each having independent entry ports (not shown) for insertion and deployment of up to 5 independent medical devices and/or injection/aspiration through the device, either simultaneously or individually.

As shown in FIGS. 1A, 1C-1D, 2A-2E, and FIG. 10A, the elongate body member 200 can be tapered at the distal end 204. This shape is particularly suitable for use in, for example, accessing the heart through the chest through the pericardium. However, the distal end can be provided with other shapes such as, for example, rounded, square, beveled/angled, and pigtailed. In addition, in some embodiments, the tip can be angled or beveled at an angle of 10°, at 20°, at 30°, at 40°, at 50°, at 60°, at 70°, or at 90° or any angle in between these angles.

Figure 6:
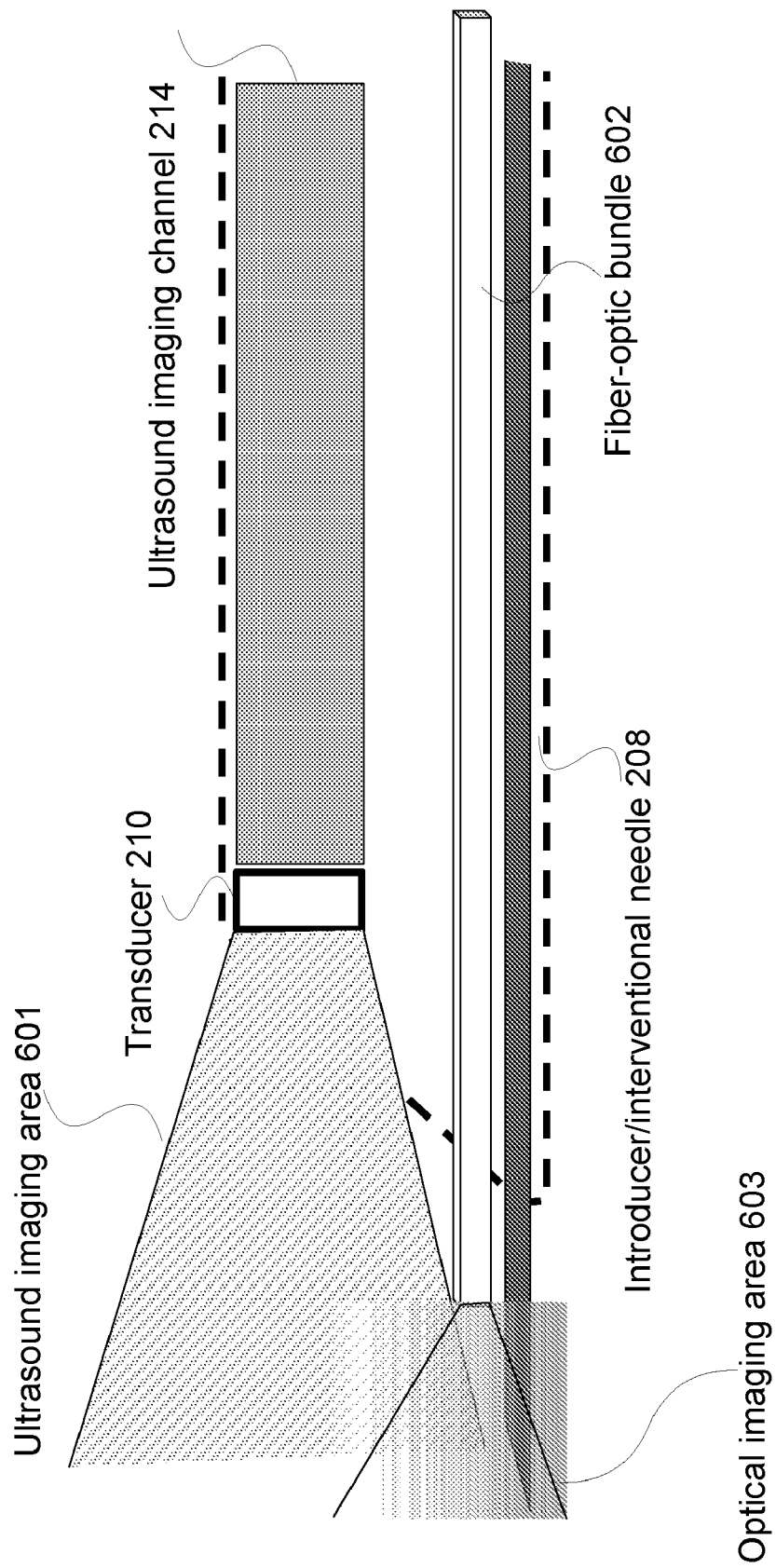
FIG. 6 depicts a device having both ultrasound and fiber optic imaging in accordance with one or more aspects described herein.

Device 100 can incorporate an imaging system that provides a user with visualization within the body during a procedure. The imaging system is particularly useful in minimally invasive procedures wherein direct visualization of the target site is unavailable. In some embodiments of a device in accordance with one or more aspects described herein, for example, as shown in FIGS. 1A, 3A, and 7A, 10A, 11A, 11B, and 12A-12E, the imaging system can be in the form of an ultrasound system comprising one or more ultrasound transducers and an imaging channel. In other embodiments, for example, as shown in FIG. 6, an imaging system can include an ultrasound imaging system combined with a fiber optic imaging system to provide additional imaging capabilities.

Ultrasound and fiber optic systems are well-known and, thus, although these systems may be described and shown with reference to a particular embodiment, the general features and components of an ultrasound system or fiber optic system that can be used in a device as described herein may be in accordance with conventional features for such systems.

As shown in FIGS. 1A, 1C, 1D, 3A, 6, 7A, 7B, 11A, 12A-12E, 16A, and 16B, the imaging system can include one or more ultrasound transducers 210 that are positioned on the elongate body 200. In one or more embodiments of an imaging interventional device in accordance with aspects and features described herein, one or more transducers 210 can be positioned at a distal end 204 of the elongate body 200 to provide imaging to a user as the device is guided to a treatment site. In addition, transducers 210 can also provide imaging functionality such that when the device is properly inserted and positioned at the target site, one or more transducers 210 can provide images of the target site.

In general, a single transducer 210 is operated at any given time. In some embodiments, a plurality of transducers 210, having different specifications as desired, can be provided on a device at various locations to provide a user with various imaging capabilities. For example, front-facing transducers as described in more detail below with respect to FIG. 5 can be provided either alone or in combination with side-facing transducers to provide a user with the capability to view structures in front of the device as well as to the sides of the device. Further, different sized and types of transducers can provide a user with various imaging capabilities (e.g. different sized views, more or less precision, etc.).

As described in more detail with respect to FIG. 5, transducers 210 can be of a size and composition in accordance with conventional transducers. For example, in some embodiments, the transducers 210 can comprise natural piezoelectric materials such as quartz, topaz, or tourmaline group minerals or can comprise man-made materials such as PZT ceramics or piezoelectric polymers such as Polyvinylidene fluoride (PVDF). Transducers 210 can also be of any suitable size, with such size being limited by the desired size of the elongate body 200 and the use which is being made of the ultrasound, i.e., for imaging or therapeutic purposes. In addition, as transducer size is decreased, the quality of the image provided also generally decreases. Thus, the smallest sized transducer that provides adequate imaging is generally used so as to minimize the required size required of the elongate body 200. For example a 2-3 mm×2 mm transducer will generally be used with an elongate body of 5-6 Fr. In certain embodiments, the transducers 210 have a maximum dimension of 5 mm, in other embodiments 4 mm, in other embodiments 3 mm, and in other embodiments 2 mm.

The transducers 210 can generally be mounted or attached to the elongate body 200 by providing one or more mounting aperture (not shown) in which the transducers 210 can be fit and held by a friction. Various adhesives can further be used to hold the transducers 210 in place.

Conducting elements 212, which can control one or more transducers 210, can extend from the transducers 210 to the proximal end 202 of the elongate body 200 and can connect to an external system (ultrasound scanner) such as a gray scale color two-dimensional Doppler ultrasound system. Conducting elements 212 can cause the transducer to emit the sound waves and transmit sound waves reflected from tissues and structures to an ultrasound scanner where they can be transformed into a digital image. The conducting elements 212 can extend through the elongate body member 200 within one or more imaging channels 214. The imaging channels 214 can be provided in various sizes and, in exemplary embodiments, can range in size from 8-30 gauge.

As shown in, for example, FIG. 1A, FIG. 13A, 15A, 16A, an ultrasound transducer that can be used in device 100 can have a handle that can be held by an operator to facilitate manipulation of the device. As shown in FIG. 1A, the handle can be a center-mounted handle that extends outward from a longitudinal axis of the device. In an alternative embodiment, for example, as shown in FIG. 16A, the handle can be offset from a longitudinal axis of the device so that the portion of the device housing the transducer does not interfere with the portion of the device housing other instruments such as introducer needle, biopsy needle, guide wire, etc.

Figure 3A:
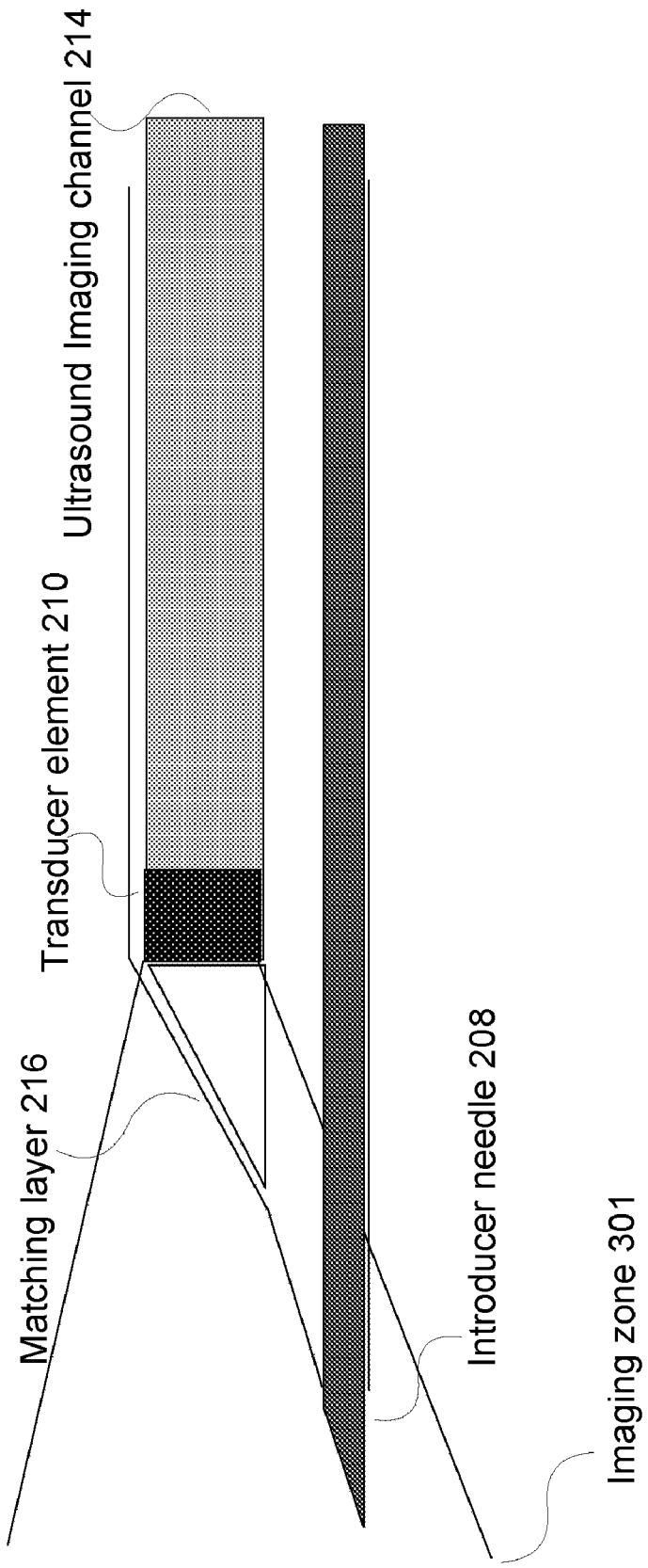
FIGS. 3A and 3B depict additional views of a patient end and an operator end of an imaging device in accordance with one or more aspects described herein.

FIG. 3A depicts a further view of a patient end of a minimally invasive imaging catheter and access instrument 200 in accordance with one or more aspects described herein. As seen in FIG. 3A, an embodiment of an access instrument as described herein can include a transducer element 210 and ultrasound imaging channel 214 integrated into a single instrument. In the embodiment shown in FIG. 3A, the access instrument includes an introducer needle 208 that is disposed to be within imaging zone 301 created by transducer element 210. To reduce ultrasound deflection during use of the device, as seen in FIG. 3A as well as in FIG. 1A, the imaging system can be provided with matching layers 216 disposed, for example, adjacent the front face of transducer element 210. Matching layers 216 can facilitate the matching of an impedance differential that may exist between the high impedance transducer elements and a low impedance patient. The structure of matching layers 216 can generally be in accordance with conventional matching layers and generally can include a matching layer front face and a matching layer rear face, and can optionally include a pocket with matching material that can reduce ultrasound deflection. Suitable matching layer materials can include, for example, plastic materials such as polysulfone or REXOLITE® (a thermoset material produced by crosslinking polystyrene with divinyl benzene, available from C-LEC Plastics, Inc., Beverly, N.J.).

The imaging system may further include a backing layer (not shown) in accordance with conventional backing layers. The backing layers can generally be coupled to the rear face of the transducers 210 and function to attenuate acoustic energy that emerges from the rear face of the transducers 210. Generally, such backing layers can have a front face and a rear face, and can be fabricated of acoustic damping material that possesses high acoustic losses.

Figure 3B:
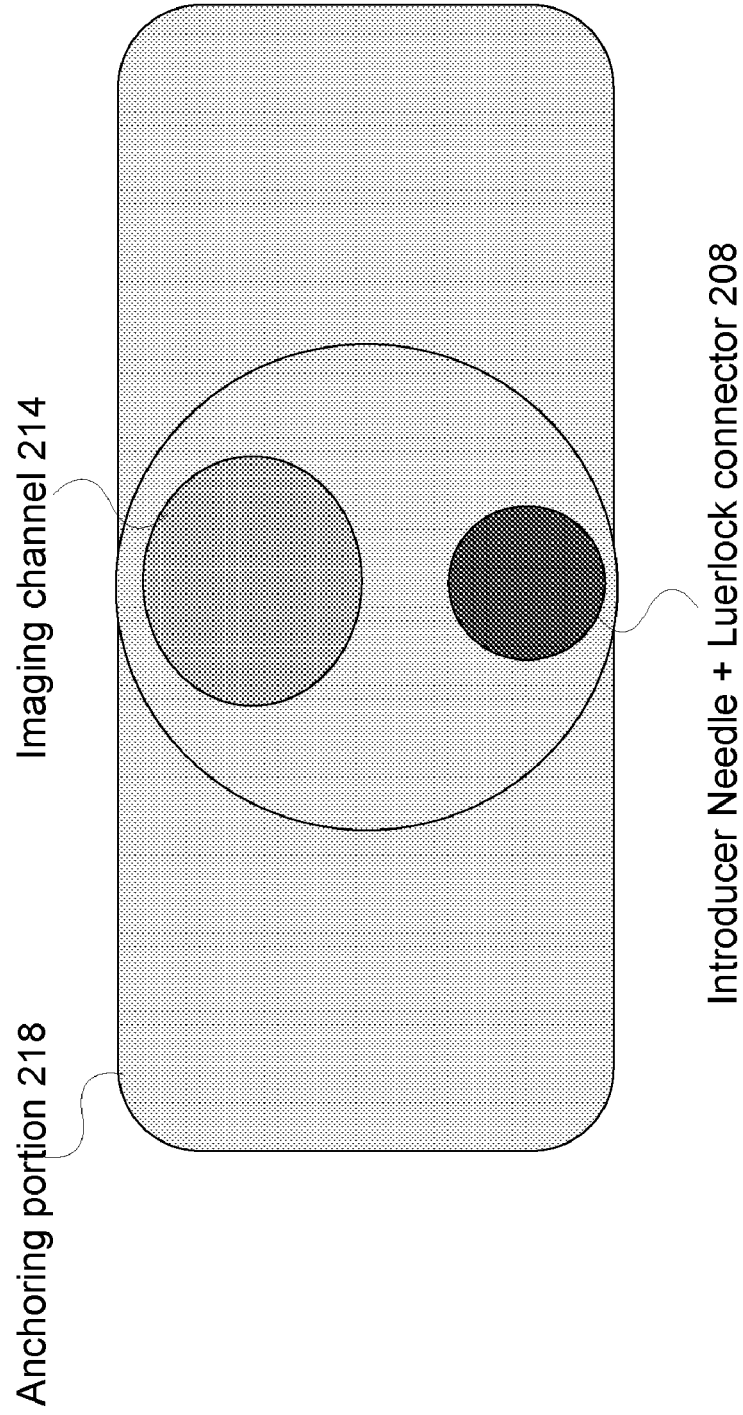

FIG. 3B shows an exemplary view of from the viewpoint of an operator end of a combined imaging and interventional device in accordance with one or more aspects described herein, for example, a device such as is illustrated in FIG. 3A. FIG. 3B shows an anchoring portion 218 of a device 100 in accordance with one or more aspects described herein. Looking towards the proximal end of the device, an operator can see two channels in the device, for example, an imaging channel 214 and a channel 208 that can accommodate an introducer needle 208, either alone or in conjunction with a Luer lock 222 such as discussed above with respect to FIG. 1A.

As seen in FIG. 4A, the distal end 202 of the body member 200 can be provided with one or more side apertures 224 in connection with the one or more lumen 206. Alternatively, as seen in FIG. 4B, the distal end of the body member 200 can be provided with one or more end-on apertures 224 to accommodate one or more lumen 206*l*. The one or more of the apertures 224 can be provided with the same or varying diameters. The apertures 224, in connection with one or more lumen 206, can be used for injection and withdrawal of materials and insertion of various instruments (needles, guide wires, biopsy devices, etc.) In some embodiments, each aperture 224 can be associated with its own lumen 206, while in other embodiments, one or more apertures 224 can share a one or more common lumen 206.

As noted above, embodiments of an imaging interventional device in accordance with one or more aspects described herein can have one or more ultrasound transducers as an integral part of the device to provide imaging capabilities to the user. FIGS. 5A-5D depict various aspects of an ultrasound transducer that can be used in a device in accordance with aspects described herein.

Figure 5A:
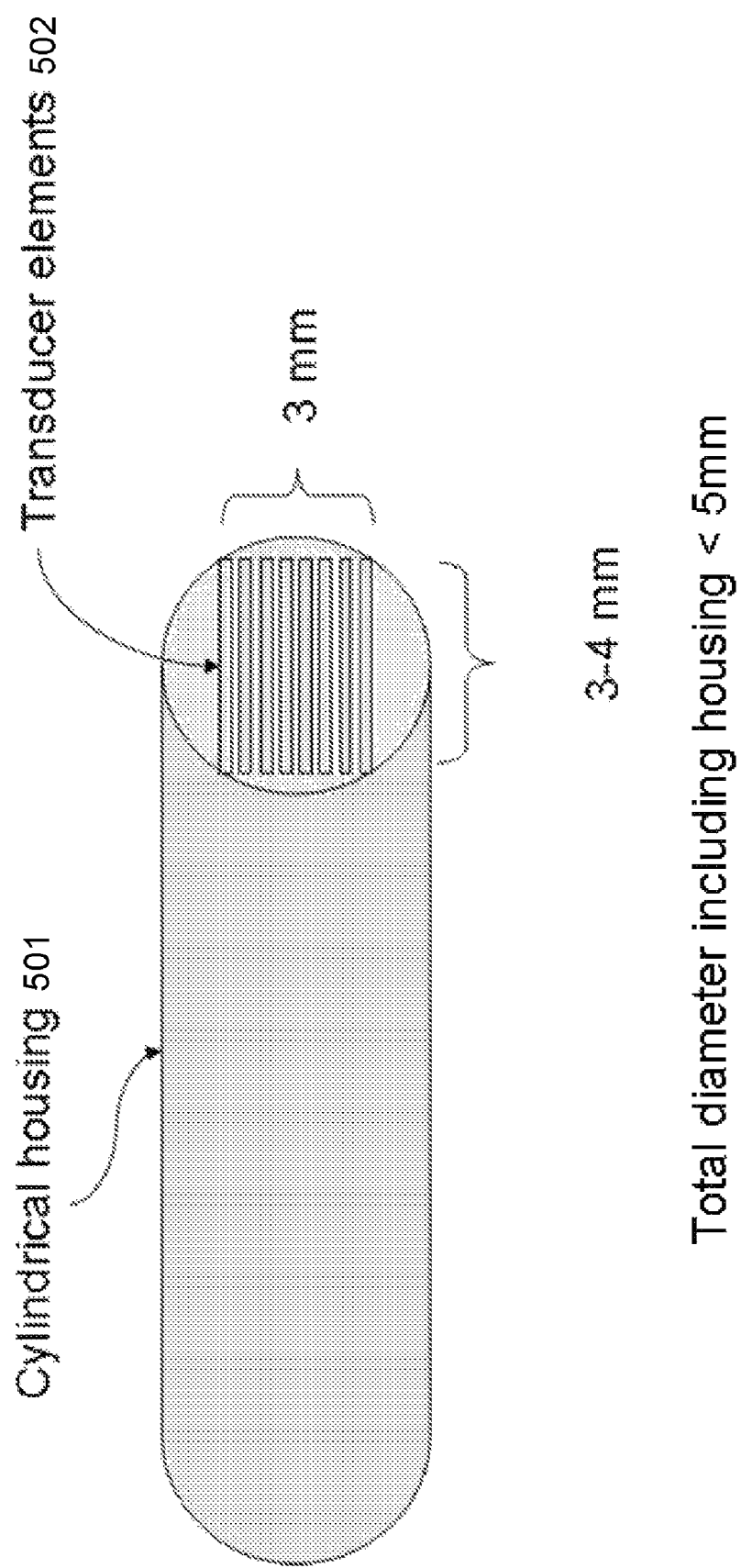

As shown in FIG. 5A, a forward projecting small ultrasound transducer such as transducer 210 shown, for example, in FIG. 1A and FIG. 3A, can comprise a cylindrical housing 501 and a plurality of transducer elements 502. In some embodiments of a device as described herein, the plurality of transducer elements can comprise a phased array transducer known in the art, while in other embodiments, the plurality of transducer elements can comprise a linear array transducer.

In an exemplary embodiment of a forward projecting small ultrasound transducer shown in FIG. 5A, the plurality of ultrasound transducer elements can be a series of rectangular elements having an approximate exemplary length of 3-4 mm and arranged in a parallel row for an exemplary total height of approximately 3 mm on a face of a transducer whose total diameter, including the housing, is less than 5 mm. As noted above, these dimensions are exemplary only, and should not be taken as providing an upper or lower limit of the dimensionality of an ultrasound transducer as described herein.

FIGS. 5B and 5C depict two exemplary embodiments of housing design options for a small ultrasound transducer such as transducer 210 in accordance with aspects described herein. As shown in FIGS. 5B and 5C, a plurality of small ultrasound transducer elements can be placed towards a front/imaging end 503 of a small ultrasound transducer to provide forward-directed imaging capabilities for an interventional device as described herein. As seen in FIGS. 5B and 5C, a housing 501 for an ultrasound transducer component that can be integrated into an interventional device as described herein can have either a flat face as shown in FIG. 5B or a rounded face as shown in FIG. 5C.

FIGS. 5D and 5E depict additional aspects of a forward-directed small ultrasound transducer such as transducer 210 for use in a device as described herein. A forward-directed small ultrasound transducer can be either cylindrical, with a round face, as shown in FIG. 5D, or more oblong in shape, with an ellipsoid face, as shown in FIG. 5E. As shown in FIG. 5D, an exemplary cylindrical transducer in accordance with one or more aspects described herein can have a round face having a diameter of 4-5 mm and a plurality of small transducer elements 502 arranged in a row along the central axis of the face. Similarly, as seen in FIG. 5E, an exemplary oblong transducer can have an ellipsoid face having a major axis length of approximately 5 mm, a minor axis length of approximately 4 mm, and a plurality of small transducer elements 502 arranged in a row along one axis of the ellipsoid. It should be noted that although in the embodiment illustrated in FIG. 5E, the elements are arranged along the major axis, in practice the small transducer elements can be arranged on either the major or the minor axis as may be desirable for a particular use or functionality. It should also be noted that described dimensions are merely exemplary and are not intended to be either minimum or maximum dimensions, of a transducer housing that can be used in a device as described herein.

As noted above, FIG. 6 depicts an embodiment of device 100 having combined ultrasound and fiber optic elements. As shown in FIG. 6, a device as described herein can have an ultrasound transducer 210 and an ultrasound imaging channel 214 which provides an ultrasound imaging area 601, and can also have a fiber optic bundle 602 which provides an optical imaging area 603. For example, ultrasound transducer 210 can be focused to provide imaging of one portion of the target area while fiber optic bundle 602 can be focused to provide imaging of another portion of the target area. The combination of fiber optic capability with ultrasound can provide beneficial additional functionality to a device as described herein. For example, ultrasound imaging can penetrate a target to provide a view of an interior of the target area but cannot provide a view of the surface of the target. In contrast, fiber optic cannot penetrate the target but can provide a view of the surface. Thus, having a dual ultrasound/fiber optic imaging capability can allow an operator to have both an interior and a surface view, giving an operator more information, for example, regarding the target site and the treatment to be applied.

In addition, as noted above, ultrasound transducer 210 can be configured to operate at different frequencies to provide different levels of imaging or therapeutic capabilities, and these capabilities can be combined with the optical capabilities of fiber optic bundle 602 to provide a wide range of imaging and/or therapeutic functions. For example, ultrasound transducer 210 operating a frequency above 1 MHz, and in particular, in the 100-200 MHz range, can provide good imaging, but only for a very short distance, and thus combining such a high-frequency transducer 210 with a fiber optic bundle 602 can provide good imaging at a greater distance. Alternatively, ultrasound transducer 210 operating at frequencies below 1 MHz can provide therapeutic treatment such as heat therapy or ablation, and thus combining a low-frequency transducer 210 with a fiber optic bundle 602 can provide both imaging and therapy in one device.

Figure 7A:
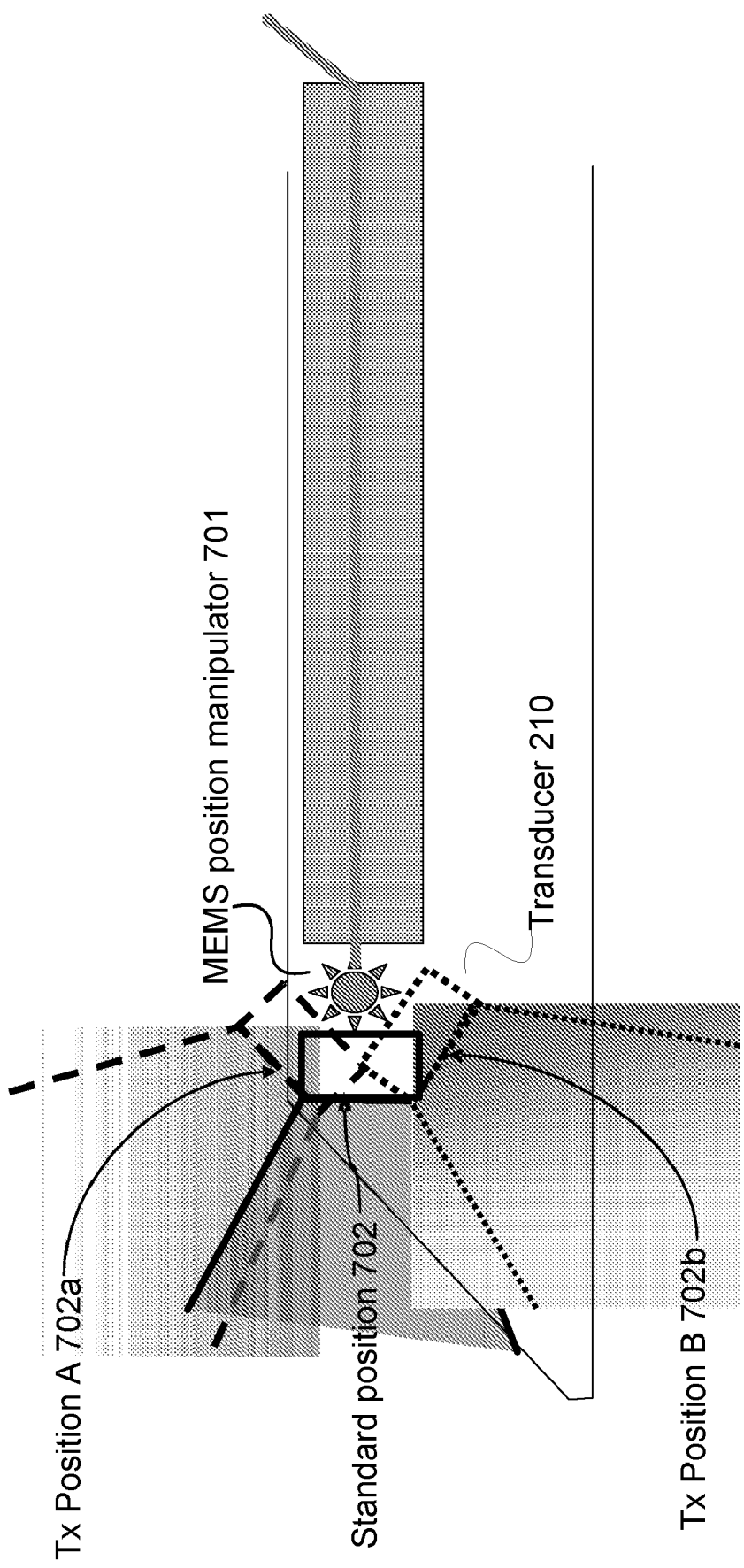

In some embodiments, device 100 can be steerable and externally controlled by the operator. For example, the distal end 204 of the elongate body 200 can be manipulated by controls located on a portion of device 100 positioned outside of the body during use. Alternatively, in some embodiments, one or more Micro-Electro-Mechanical Systems (MEMS) devices can be incorporated into de vice 100 to allow an operator to control aspects of the device. MEMS systems can include, for example, mechanical elements (beams, cantilevers, diaphragms, valves, plates, and switches), sensors, actuators, and electronics. For example, as shown in FIG. 7A, a MEMS position manipulator 701 can be mounted on device 100 at a distal portion of device 100 to control a position of transducer 210 to, for example, standard position 702, Position A 702*a* or Position B 702*b*. In other embodiments, one or more MEMS devices can be provided to function as tiny sensors and actuators. For example, MEMS can be incorporated in the device for measuring and monitoring pressure in the stomach or other organs in which the catheter is inserted, and for measuring and monitoring blood pressure when performing cardiac catheterization.

In another embodiment, for example, as shown in FIG. 7B, a MEMS manipulator lead fixation device 703 can be provided to permit an operator to remotely access a portion of a device within a patient's body. For example, MEMS manipulator 703 can be used to screw in a lead for a pacemaker implanted in a patient. Alternatively, MEMS manipulator 703 can be used to operate a biopsy needle or to manipulate a suture-application device within a patient. It should be noted that these uses are exemplary only and that a device having a MEMS manipulator as described herein can be used to access or manipulate any device in a body or for any other suitable purpose.

In accordance with aspects described herein, a device 100 having a biopsy instrument such as that depicted in FIGS. 8A-8D. In such an embodiment, device 100 can be adapted for use in biopsy procedures including but not limited to myocardial biopsy, brain biopsy, muscle biopsy, lung biopsy, liver biopsy, kidney biopsy, uterine and ovarian biopsy, esophageal biopsy, stomach biopsy, intestinal biopsy, tumor biopsy (anywhere), targeted biopsy of potentially abnormal zones in any of the above items (e.g., ultrasound guided biopsy of an abnormal area in the liver or kidney with the present catheter will allow access to the abnormal area, identification of abnormal zones by deploying the ultrasound and biopsy instrument to the specific area of interest). As such, device 100 can, in some cases, be in the form of a catheter or sheath-like device that is insertable through small incisions in the body. The sheath-like device could include one or more lumen 214 through which a biopsy tool could be inserted. Device 100 in the form of a sheath could, thus, be provided along its length, as set forth above, with one or more ultrasound transducers 210 along with the other components required to provide ultrasound imaging using the transducers 210.

Figure 8A:
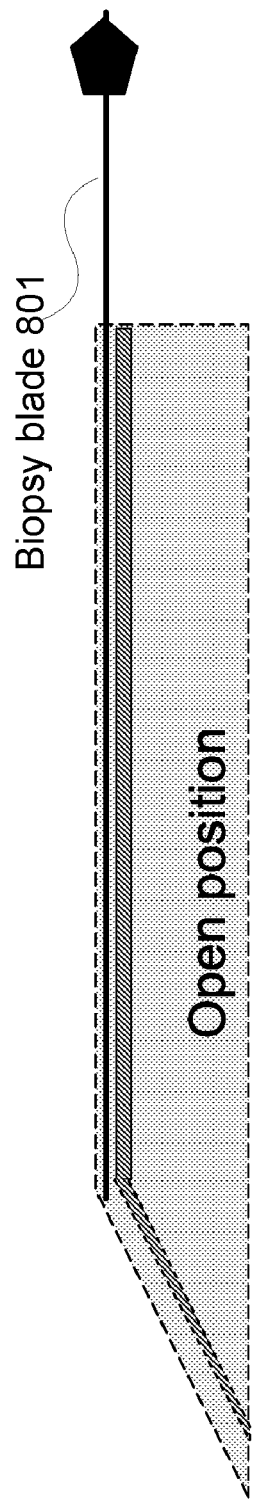
FIGS. 8A-8D depict embodiments of a biopsy instrument that can be used in a minimally invasive device in accordance with one or more aspects described herein.
Figure 8B:
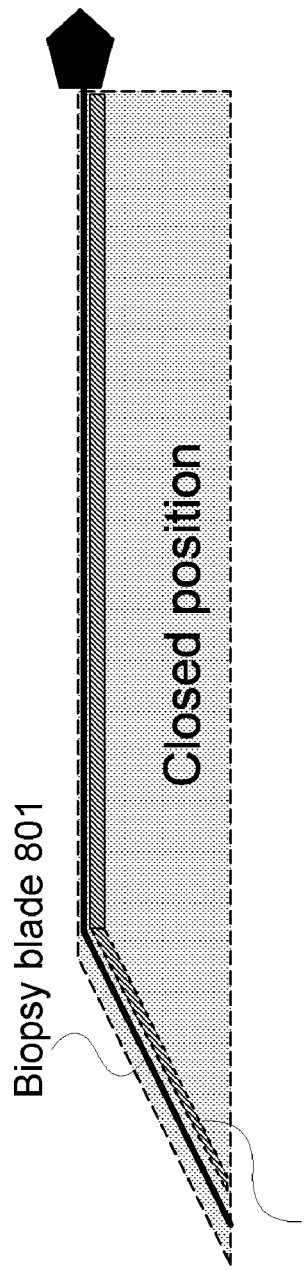
Figure 8C:
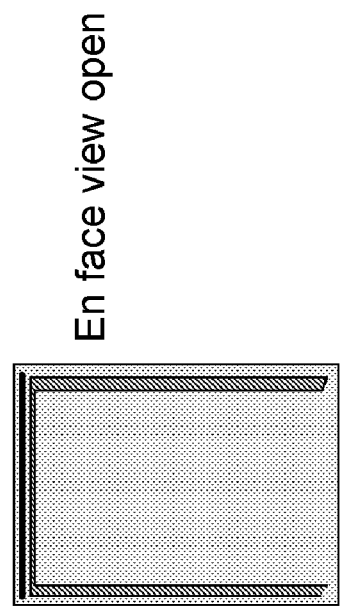
Figure 8D:
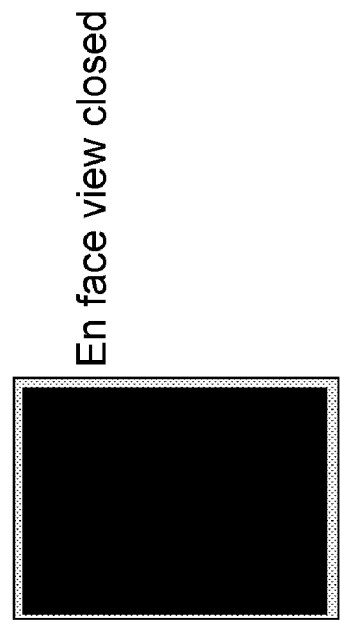

In another case, device 100 could itself be a biopsy tool (either a minimally invasive biopsy tool that is insertable through a sheath or a biopsy tool that is directly insertable within the body). In this embodiment, for example, as shown in FIGS. 8A-8D, the distal portion of the biopsy tool could include the mechanism for obtaining a biopsy (tissue sample) as well as one or more transducers 210, along with the other components required to provide ultrasound imaging using the transducers 210 as discussed herein. As shown in FIGS. 8A and 8B, a biopsy blade 801 in an open position can be disposed, for example, in a lumen 206 of device 100. As seen in FIGS. 8A and 8C, a needle with biopsy blade 801 in open position can be inserted into the body and then closed as shown in FIGS. 8B and 8D to remove a portion of tissue for testing.

In another embodiment, such as is shown in FIGS. 9A and 9B, device 100 can include a retrieval instrument in combination with a bioptome or other custom instrument 903. As is known in the art, a bioptome can comprise a specialized biopsy catheter for use in cardiac applications, particularly a catheter with a special end designed for obtaining endomyocardial biopsy samples. In use, a bioptome can be threaded through a guiding catheter such as an imaging catheter in the form of device 100 to the right ventricle, where it can snip small tissue samples from the septal wall for pathologic examination. In other uses, a bioptome tip device can be used to monitor heart transplantation patients for early signs of tissue rejection. In use, as seen in FIGS. 9A and 9B, a retrieval instrument having a bioptome 903 can be in closed position 901 at a distal end and closed position 904 at a proximal end to assist in inserting the instrument into the area of interest, and then can be placed into an open position 902 at the distal end so that the desired tissue can be retrieved for examination or testing.

Figure 10A:
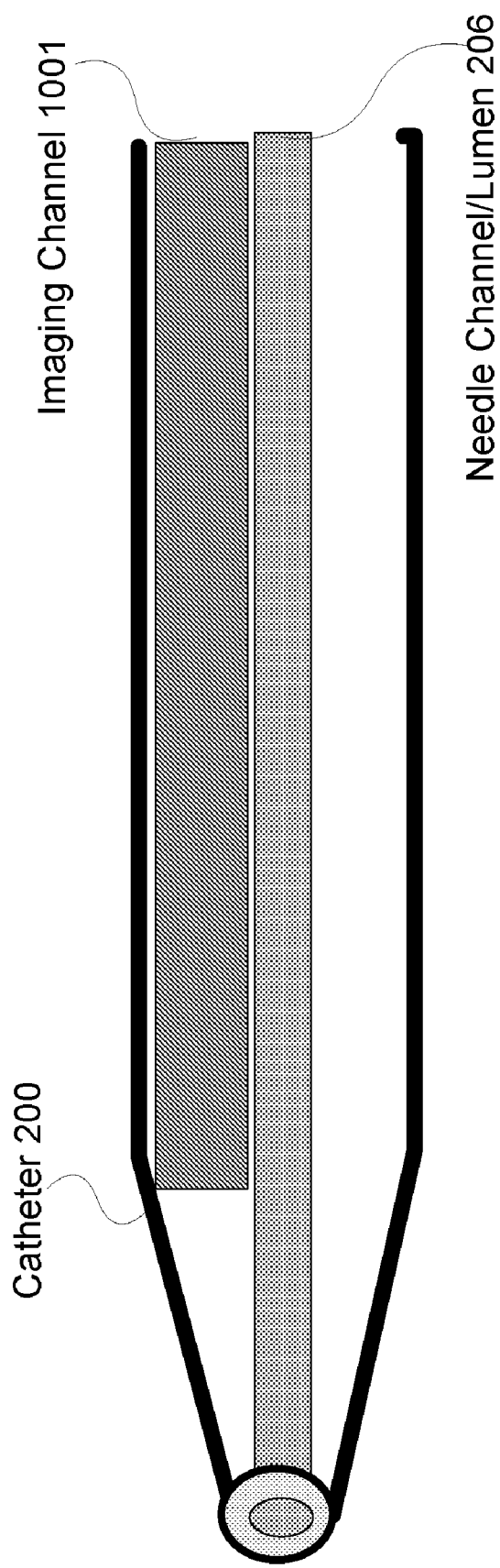

FIG. 10A-10C depict an additional embodiment of device 100 in accordance with aspects and features described herein. It can be appreciated that configuration of device 100 can be customizable as may be appropriate for a particular therapeutic application or for use at a particular site. For example, device 100 can be long and slender or shorter and wider, depending on the use to which it is put. In addition, it may be desirable to place device 100 at a target site under imaging guidance, for example, using one or more ultrasound transducers 210, and then remove the transducer and insert instead a different transducer 210 for use at the treatment site. For example, a transducer at one frequency may provide one type of imaging capability such as lower-frequency, lower-resolution ultrasound imaging at greater depth, which may be useful to place the device, whereas higher-frequency, higher-resolution ultrasound imaging at a shorter distance may be more desirable once the device is in place and treatment begins. Alternatively, ultrasound at an even lower-frequency than that used to guide the device to the target site may be desirable for therapeutic uses, such as to provide heat to tissue or to permit ablation of tissue from the target site.

In another embodiment, the second, replacement transducer can have other different properties than the first one. For example, the second transducer can be of different dimensions, in length, in diameter, or both, than the first transducer, as may be appropriate for use at the treatment site. Alternatively, the second transducer can be made of a different material having different properties. For example, the second transducer can be of a smaller diameter and/or more flexible than the first as may be appropriate to permit the device to be placed at the target site.

In addition, it can be appreciated that a device 100 can become damaged or contaminated by body fluids during use and therefore must be discarded after the procedure.

Consequently, it can be advantageous to provide a device having an ultrasound transducer that can be interchangeably placed within or removed from an outer sheath as may be desirable. In the case where the device 100 is discarded after the procedure, this can enable the outer sheath to be discarded while the transducer can be reused after being sterilized.

In the embodiment depicted in FIGS. 10A-10C, elongate body in the form of a catheter 200 can be provided without an ultrasound transducer element but instead with an empty imaging channel 1001 into which a transducer element can be placed to provide an imaging catheter as described in more detail above. Such an imaging catheter can be combined with the other aspects such as an introducer needle or one or more other interventional or therapeutic devices, for example, through needle channel/lumen 206 shown in FIG. 10A. In this embodiment, as shown in FIG. 10B, a transducer 1003 can be provided that can be configured to fit within imaging channel 1001 shown in FIG. 10A. In some embodiments, transducer 1003 can also have a protruding ridge 1004 along the length thereof and imaging channel 1001 can have a corresponding groove so that ridge 1004 can fit within the groove to provide a secure placement of transducer 1003 within imaging channel 1001. Such a configuration is shown in FIG. 1C, which shows a cross-sectional view where transducer 1003 having ridge 1004 is placed within catheter 200 having a needle channel/lumen 206.

Figure 11A:
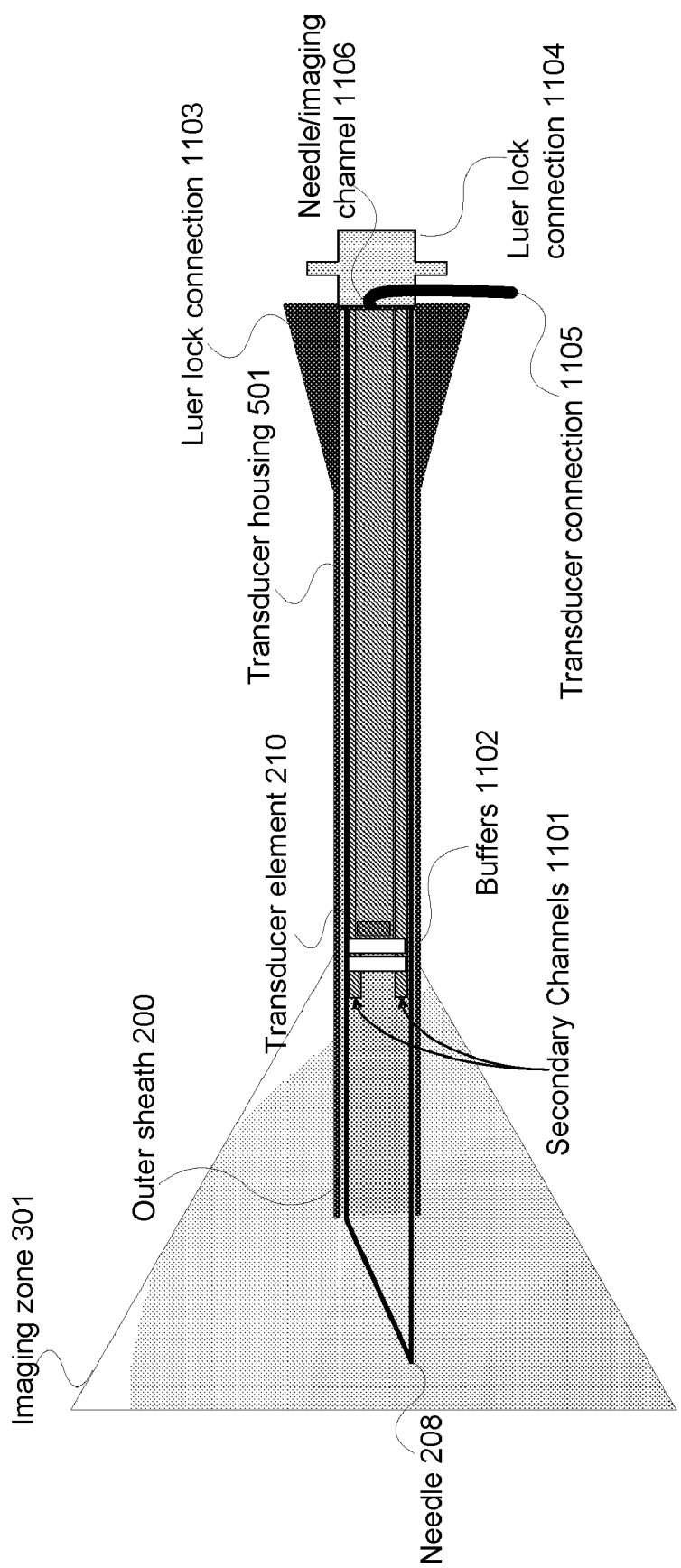
FIGS. 11A and 11B depict an embodiment of an imaging catheter wherein both a needle and an ultrasound transducer are disposed within a single needle/imaging channel.
Figure 11B:
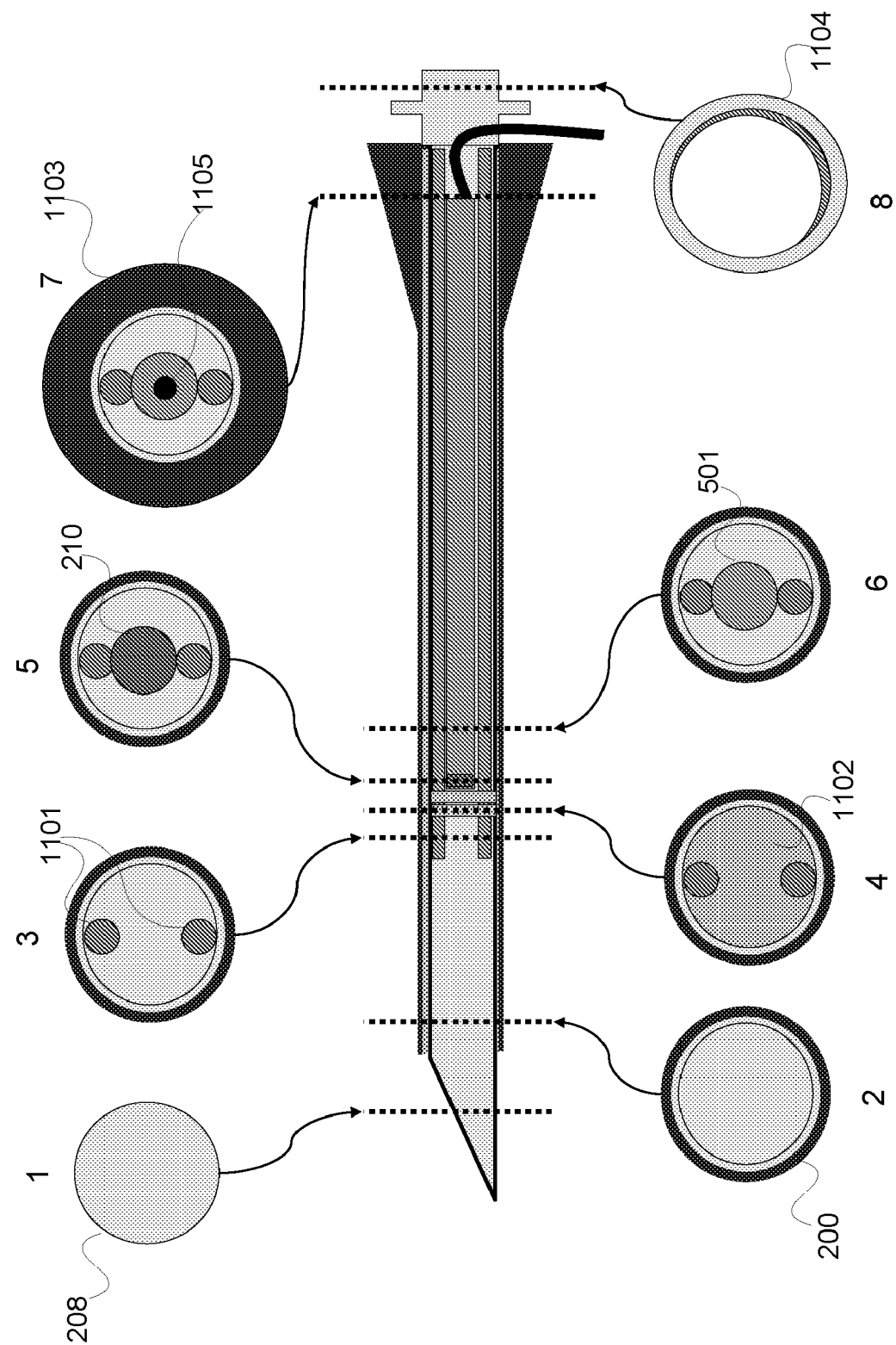

FIGS. 11A and 11B depict an embodiment of an imaging catheter wherein both a needle and an ultrasound transducer, for example, in the form of a combined needle/transducer assembly, are disposed within a single needle/imaging channel as opposed to being in parallel channels as shown, for example, in FIG. 3A. As shown in FIG. 11A, an embodiment of an imaging catheter can include an outer sheath 200 as described above, having a single channel into which can be disposed both an introducer needle 208 and a transducer element 210 having a transducer housing 501 and transducer connection 1105. These elements may collectively be referred to herein as a needle assembly. As shown in FIG. 11A, such a configuration can provide an imaging zone 301 which can be used, for example, to guide the device to the target site after having it is inserted into the body using needle 208. One or more buffers 1102 can be provided in the channel to prevent transducer element 210 from coming into direct contact with, and thus possibly being damaged by, needle 208. In addition, a device as shown in FIG. 11A can be provided with a Luer lock hub 1103 on the sheath, alone or in conjunction with a Luer lock connection 1104 on needle 208, for example, for a syringe attachment (not shown).

In addition, one or more channels 1101 can be provided around the needle/imaging channel to provide access for a guide wire or to provide a channel for the delivery or withdrawal of fluids. In an embodiment of a device in accordance with aspects herein, channels 1101 can be used to provide fluids such as a saline solution to assist in the delivery of the device to the target site or to provide fluids such as therapeutic drugs to the target site. Alternatively, channels 1101 can be used to house a dye or other imaging aid within the catheter body itself so that the device can be viewed by external imaging means. For example, as is known in the art, a saline solution appears cloudy when viewed by external imaging means and thus having a saline solution disposed in one or more of channels 1011 can assist an operator to view the device as it travels through the body or once it reaches the target site.

FIG. 11B depicts cross-sections along the length of a device as shown in FIG. 11A. For brevity and clarity in the Figure, only additional elements at each stage along the length of the device are denoted by reference numbers. As shown in FIG. 11B, cross section 1 shows needle 208. Cross section 2 shows needle 208 and an outer ring denoting catheter/sheath 200. At cross-section 3, there is shown needle 208 and outer sheath 200, plus channels 1101 described above with reference to FIG. 11A. Cross-section 4 shows all the elements shown in cross-section 3, plus a face of a buffer 1102 described above with reference to FIG. 11A. Cross-section 5, which is taken on the other side of buffer 1102 does not show a face of a buffer 1102 or needle 208 but instead shows a face of a transducer element 210 along with an outer ring depicting outer sheath 200 and channels 1101 described above. At cross-section 6, there is shown transducer housing 501, which houses transducer connection 1105, with channels 1101 and outer sheath 200. Cross-section 7 depicts the device at the level of Luer lock hub 1103, and shows an outer ring denoting Luer lock connection on the outer sheath. In accordance with one or more aspects described herein, Luer lock hub is at an operator end of the catheter/sheath 200 and can be used to directly connect the device to a syringe after needle 208 is removed. Also shown are connector channels 1101 and transducer cable connection 1105, which can exit the assembly on the side through a water-tight port. The final cross-section shown in FIG. 11B, cross-section 8, depicts a Luer lock connection 1104 end of the assembly shown in FIG. 11A.

As shown in FIGS. 12A and 12B, in accordance with one or more aspects described herein, a syringe 1201 can be attached at the proximal end thereof, for example, by means of a Luer lock connection 1104. In one use, syringe 1201 can provide leverage and transmit force and torque to assist the needle in advancing through tissue to the target site. In addition, as described above, because channels 1103 also exit the catheter/sheath 200 at the proximal end, the syringe can be used to deliver liquids such as anesthetic material, saline solution, imaging dye, or drugs to the front end of the needle by means of channels 1103. Similarly, as shown in FIG. 12B, if needle 208 is advanced into a fluid-filled cavity, the fluid contents can be evacuated by suction applied to a plunger of syringe 1201.

Figure 12C:
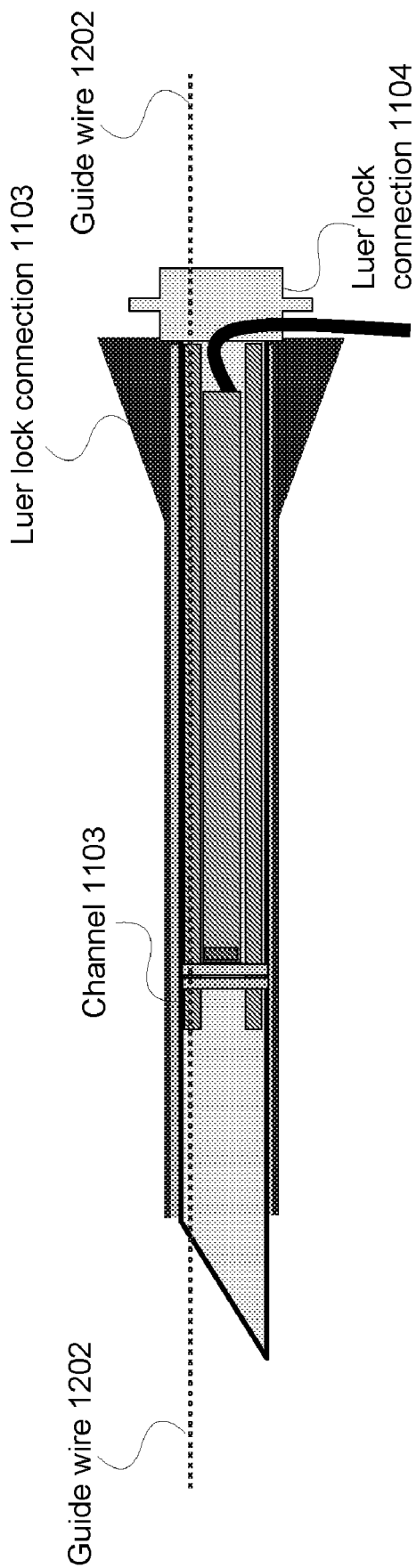
Figure 12D:
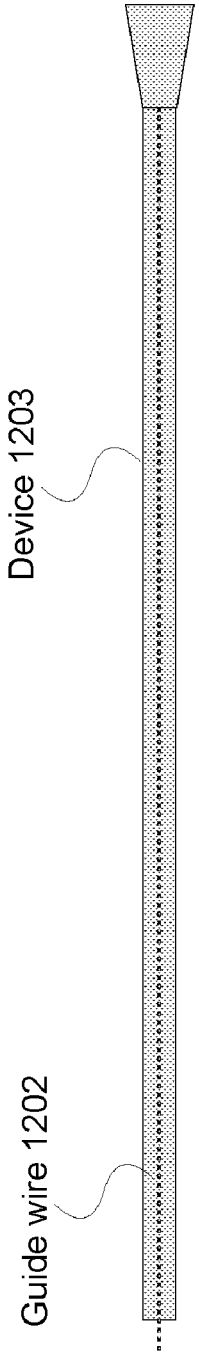

As shown in FIGS. 12C and 12D, if it is desirable that one or more additional devices be delivered to the target site, syringe 1201 can be disconnected from the catheter via Luer lock connection 1104 then the syringe is disconnected, a guide wire 1202 can be introduced through channel 1103 and out of the front end of the needle into the hollow or solid structure at the target location. In an exemplary embodiment, needle 208 can then be withdrawn, leaving guide wire 1202 in place such that the distal (patient) end of guide wire 1202 is retained in the target location. Another device such as a catheter or sheath 1203 as shown in FIG. 12D can then be threaded over this guide wire to the target location.

Figure 12E:
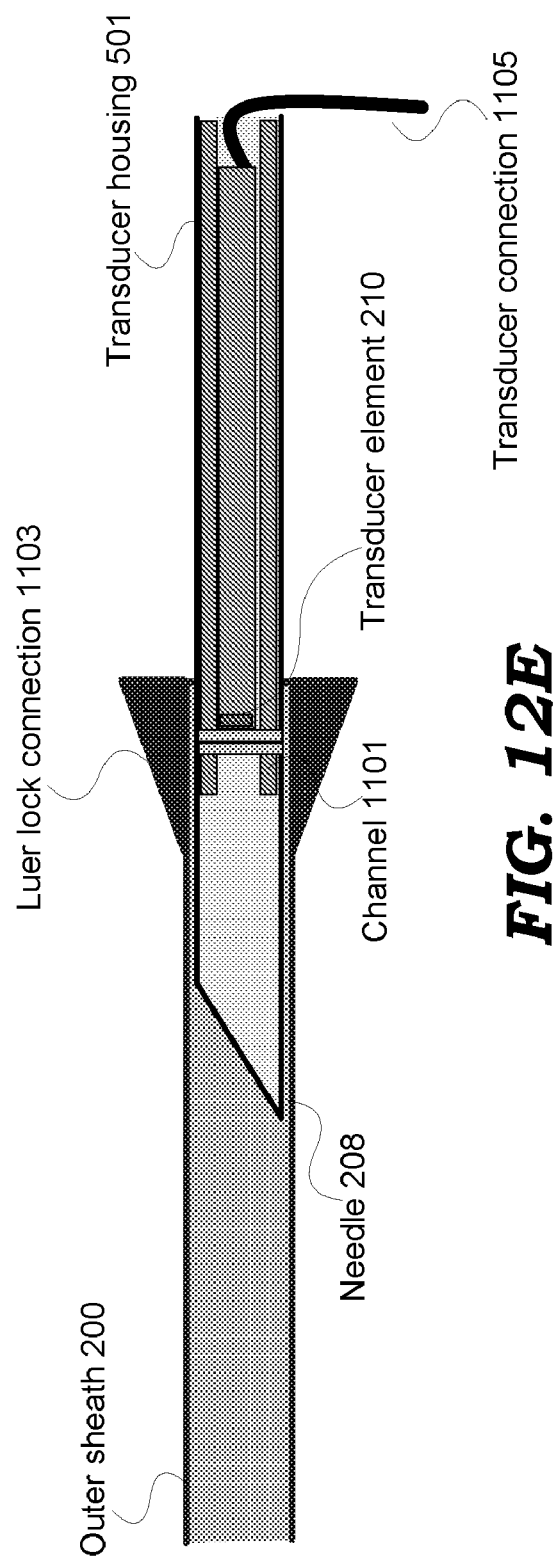
Figure 12F:
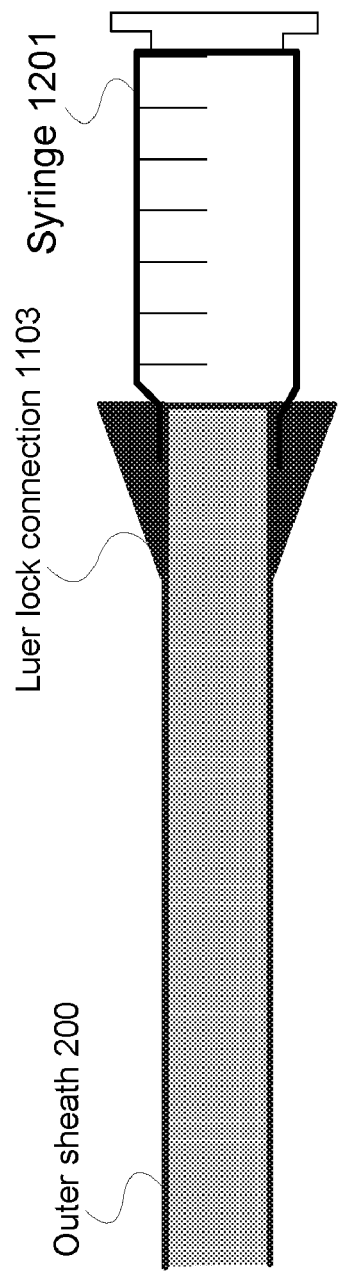

In an alternative embodiment as shown in FIGS. 12E and 12F, if no guide wire is needed and only fluid evacuation or delivery is necessary, then the sheath is advanced under vision such that the tip of catheter/sheath 200 is in the desired target location. In an exemplary embodiment, the sheath has a needle assembly as described above inserted into an opening extending through the length thereof. As shown in FIG. 12E, once the catheter reaches the target site, the needle assembly can be withdrawn, leaving the tip of the sheath in place. Syringe 1201 can then be attached to Luer lock connection 1103, and fluid can be drained from or delivered into the target location.

FIGS. 13A and 13B show two embodiments of an outer shell 224 that can be used for an integrated imaging and interventional device 100 in accordance with one or more aspects and features described herein. As noted above, an outer shell 224 of device 100 can be fabricated of materials such as silicone, Teflon, polyurethane, PVC, and elastomeric hydrogel (AQUAVENE). In an exemplary embodiment, an outer shell 224 as shown in FIGS. 13A and 13B can be configured to provide an imaging channel 1001 that can accommodate an ultrasound transducer and a needle channel 206 that can accommodate a needle to allow entry into a particular anatomic location.

In an exemplary embodiment, imaging channel 1001 can consist of two portions, one towards a distal end of the device and the other towards a proximal end. In accordance with one or more aspects described herein, the distal portion of imaging channel 1001 can be fabricated of a softer, pliable plastic or other material while the proximal portion can be fabricated of a harder, more rigid material to prevent damage to the transducer handle and keep its cable connections secure. Needle channel 206 can be fabricated completely out of a softer, pliable plastic or other similar material, except for a hub 1303 at the operator end, for example, as shown in FIGS. 13A-13D, which can be made of harder plastic. Hub 1303 can have a Luer lock or a straight connection to other devices or, for example, a guide wire at the proximal end. As shown in FIGS. 13C and 13D, in an exemplary embodiment, hub 1303 can have an overhanging edge all around needle channel 206 except for the region abutting the handle chamber 1301 in the case where the transducer has a handle or imaging channel 1001 in the case where the transducer does not have a handle.

Figure 14A:
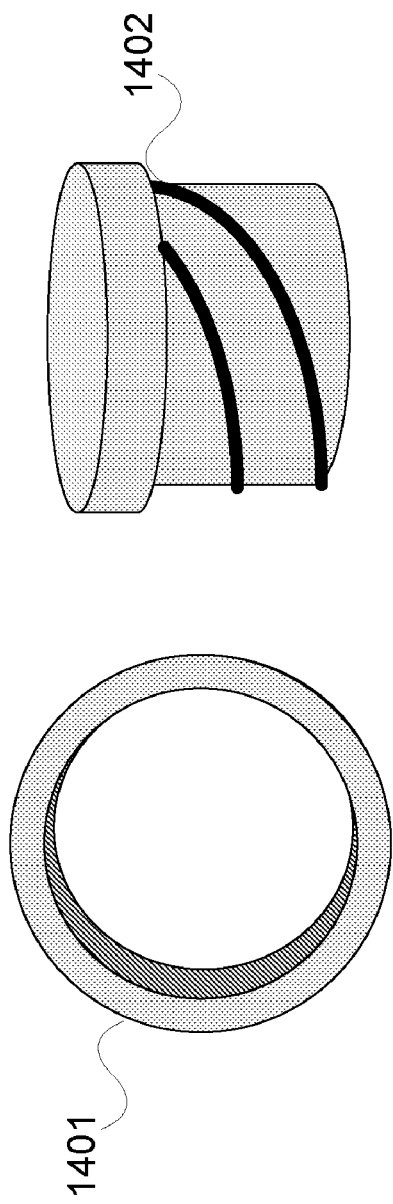
FIGS. 14A-14E depict embodiments of a locking mechanism that can be used with an outer shell of an imaging catheter in accordance with one or more aspects described herein.
Figure 14C:
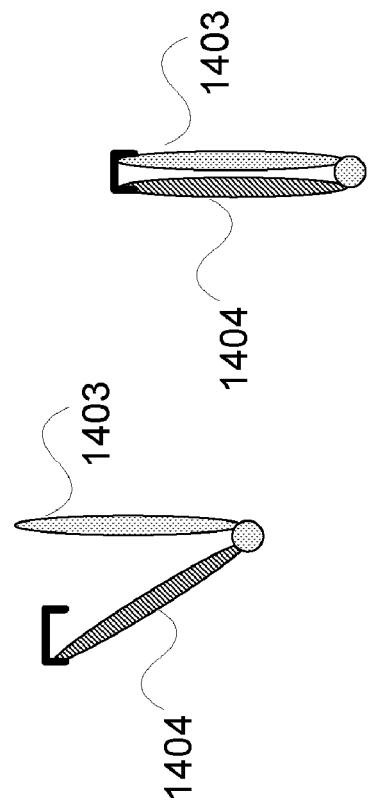
Figure 14B:
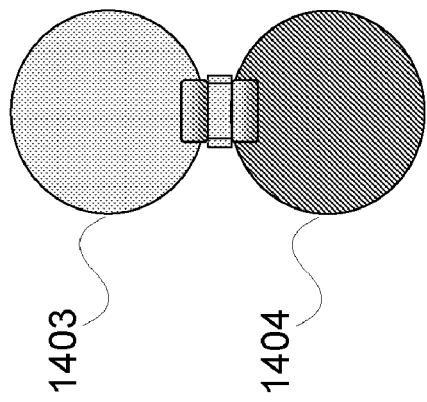
Figure 14D:
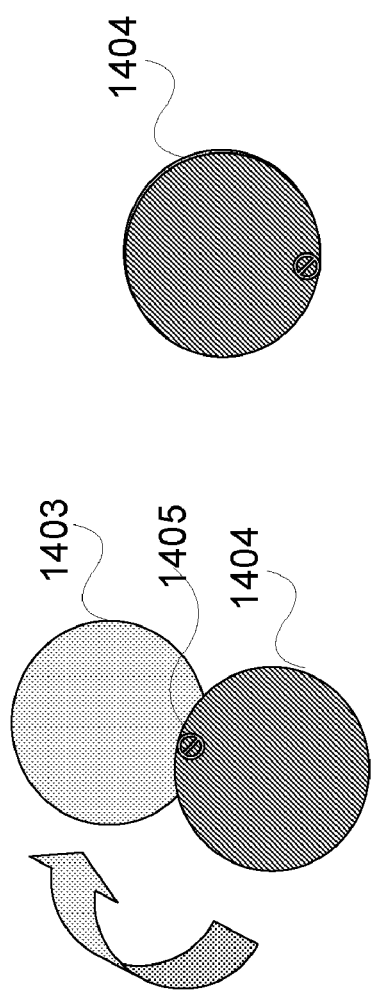
Figure 14E:
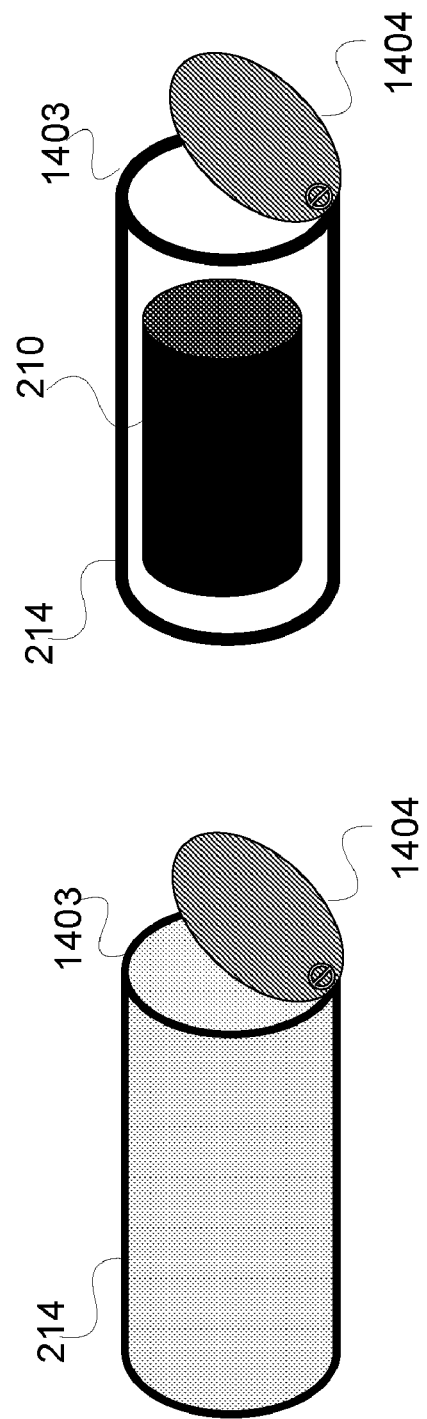

In certain embodiments, an outer shell 224 for device 100 can have a cap or other locking component 1302 for placement over a proximal end of the housing to secure the transducer position within imaging channel 1001 so that it does not rotate or slide out of position during use. Some exemplary configurations of cap or locking component 1302 are shown in FIGS. 14A-14E. FIG. 14A shows a screw-type cap, wherein cap 1402 can screw into a screw mount 1401. An alternative embodiment of a cap is shown in FIG. 14B, which includes a cap portion 1404 that can cover an opening 1403 in handle chamber 1301 shown in FIG. 13A. As shown in FIG. 14C, cap 1404 can lock into place to cover opening 1403 and secure the transducer. In the alternative embodiment shown in FIG. 14D, lid 1404 can be rotated around pivot point 1405 close over opening 1403. As shown in FIG. 14E, lid 1404 can be closed over opening 1403 in imaging channel 214 either with or without the presence of ultrasound transducer element 210 being secured within.

FIGS. 15A and 15B depict embodiments of an opening in the outer housing to accommodate an ultrasound transducer cable used in a device according to aspects and features described herein. 15A depicts an embodiment wherein the outer shell is configured to accommodate an ultrasound transducer having an offset handle as described above. In the embodiment depicted in FIG. 15A, the transducer handle can reside in handle chamber 1301 with the ultrasound transducer in imaging channel 1001 secured by locking element lid 1404, and the cable 1503 for the ultrasound transducer can extend out of a cable side port 1502 in handle chamber 1301. The embodiment depicted in FIG. 15B is similar, but is configured to house an ultrasound transducer element not having an offset handle. In this embodiment, as in the embodiment shown in FIG. 15A, the ultrasound transducer can reside in imaging channel 1001 secured by locking element lid 1404, with transducer cable 1503 extending out of cable side port 1502 in imaging channel 1001. In either embodiment, use of a side port for an ultrasound transducer cable will allow the cable to exit the device without impeding the locking mechanism or otherwise reducing the secure position of the transducer within imaging channel 1001.

FIGS. 16A and 16B depict embodiments of a complete device assembly in accordance with one or more aspects and features described herein. As shown in FIG. 16A, a device 100 in accordance with aspects herein can include an outer shell 224, for example, as described above with respect to FIG. 13A, having an ultrasound transducer 210 disposed within an imaging channel 1001 and a needle 208 disposed within a needle channel 206. In the embodiment of device 100 shown in FIG. 16A, transducer 210 has an offset handle 1602 disposed within handle chamber 1301 and is secured within imaging channel 1001 by means of lid 1404. Needle channel 206 has a needle channel hub 1303 that can abut a needle hub 1601, for example, to provide a smooth transition area between needle channel 206 and a needle hub 1601 at a proximate end of needle 208. Cable 1503 extends from a port in handle chamber 1301, for example, as described above with respect to FIG. 15A.

FIG. 16B similarly depicts an embodiment of device 100 according to aspects described herein, in a case where transducer 210 does not have an offset handle 1602. In the embodiment shown in FIG. 16B, device 100 can include an outer shell 224 having an ultrasound transducer 210 disposed within an imaging channel 1001 and a needle 208 disposed within a needle channel 206. Transducer 210 is secured within imaging channel 1001 by means of lid 1404 and has cable 1503 extending from a port in imaging channel 1001, for example, as described above with respect to FIG. 15B. As in the embodiment shown in FIG. 16A, needle channel 206 has a needle channel hub 1303 that can abut a needle hub 1601, for example, to provide a smooth transition area between needle channel 206 and a needle hub 1601 at a proximate end of needle 208.

Figure 17:
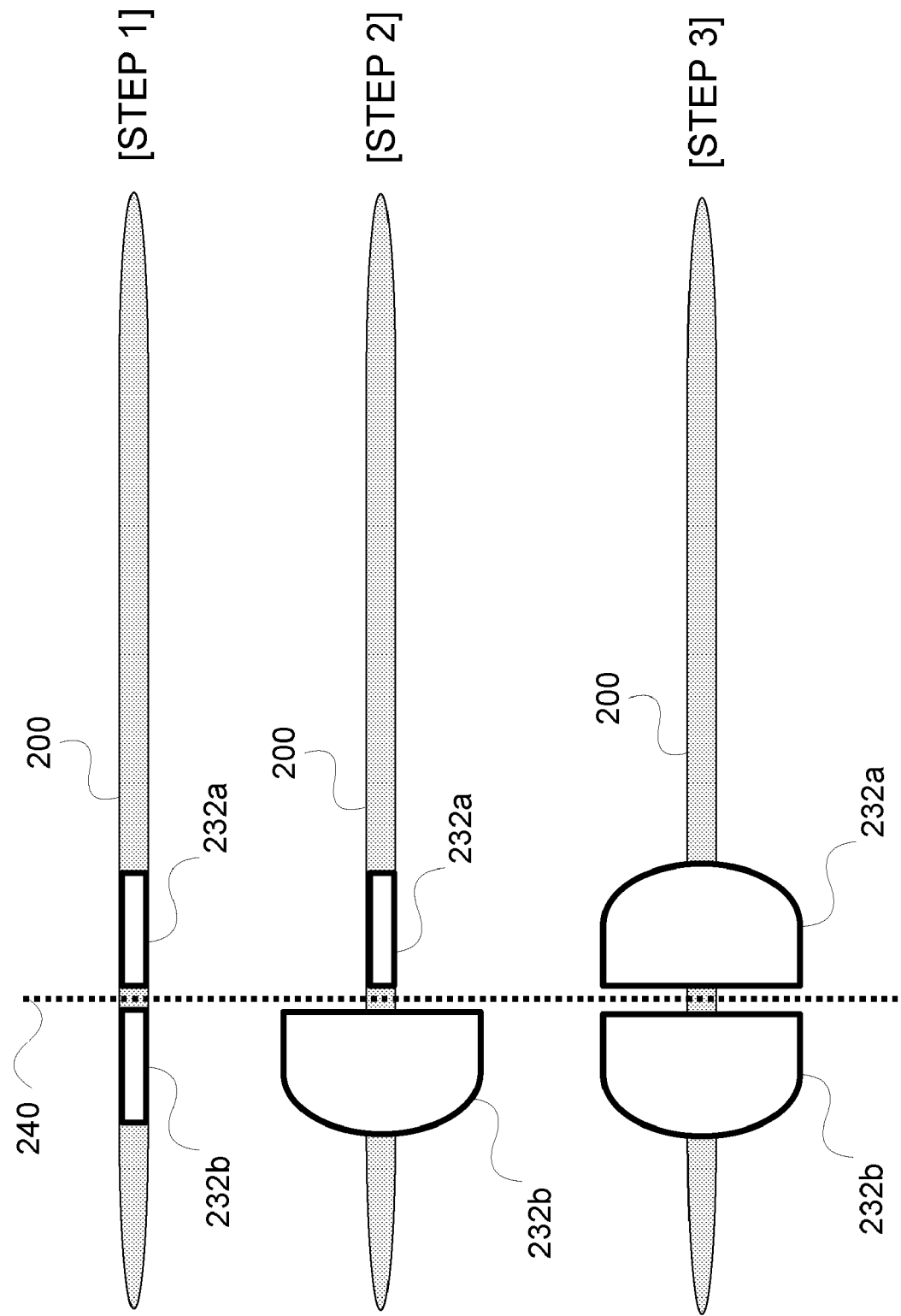
FIG. 17 illustrates aspects of an exemplary dual-balloon cardiac procedure that can be performed with an interventional medical device configured in accordance with one or more aspects described herein.

FIG. 17 depicts an embodiment of an exemplary cardiac procedure that can be performed using a device 100 as described herein. This procedure is described only to give an example of an advantageous use that can be made of a device having one or more of the features described herein, and is not intended to be in any way limiting of the type or scope of procedures for which a device as described herein can be used. This exemplary procedure involves the use of device 100 to insert and deploy two balloons within a patient's pericardium to anchor the device to the pericardial wall so that additional interventional or therapeutic instruments can be guided into the pericardium so that the patient can be treated. Thus, in the embodiment shown in FIG. 17, a distal balloon 232b and a proximal balloon 232a can be disposed within elongate body 200. In an exemplary procedure, the device can be inserted into the chest, for example by use of an introducer needle integrated therein, and guided, for example by use of an integrated ultrasound transducer, to the pericardium. As shown in Step 1, the pericardial wall 240 can be pierced, for example, by the needle, so that the portion of the device having distal balloon 232b extends beyond the pericardial wall into the pericardium itself. At step 2, distal balloon 232b can then be inflated, either by a saline solution or with another solution, so that it fits against the interior pericardial wall of the patient. Once distal balloon 232b is inflated, the elongate body 200 can be pulled towards the operator so that balloon 232b fits snugly against the pericardial wall, and at step 3 proximal balloon 232a can be inflated so that the elongate body 200 is secured in place within the chest. In an alternative embodiment of such a procedure, one or more of balloons 232a and 232b can be inflated using a solution bearing a contrast agent so that the device can be readily seen by MRI, CT scan or other external imaging means. More detail regarding this exemplary procedure and other procedures which can be performed using a device employing one or more aspects or features described herein is set forth in the U.S. Patent Application entitled "Image Guided Catheter Having Deployable Balloons and Pericardial Access Procedure" by Theodore Abraham, the inventor hereof, which is being filed concurrently with the present application and which is hereby incorporated by reference herein.

Device 100 in accordance with one or more aspects described herein can have many different embodiments for many different uses within the scope and spirit of the present disclosure. Device 100 can be in the form of a catheter or sheath that provides entry into these various body spaces, thus allowing therapy delivery, intervention, placement of devices and diagnostics. Device 100 can also be in the form of interventional devices for use in procedures within these spaces. Such catheters, sheaths, and devices are well known, and, thus, the general features of device 100 for these embodiments can be in accordance with conventional devices.

In addition, when provided with one or more integrated transducers 210 and other components required to provide ultrasound imaging as described herein, device 100 can be used in a wide variety of procedures which can be made substantially safer and easier through the combination of imaging aspects with therapeutic aspects of the device.

In some embodiments, device 100 can be used to provide access vascular structures including arteries, veins, lymphatics, and to other hollow structures such as the gastrointestinal tract, genitourinary tract, and the respiratory system. As such, the device can be in the form of, for example, a vascular sheath. Such sheaths are well known, and, thus, the general features of device 100 for these embodiments can be in accordance with conventional devices. Device 100 could further include one or more transducers 210, along with other components used to provide ultrasound imaging using the transducers 210 as discussed herein.

In other embodiments, device 100 can be used in procedures in various body spaces such as the pleural peritoneal space, pericardial space, perisphinal space, pelvis, and cerebrospinal space. For example, the device can be adapted for use in paracentesis, biopsy of any intra abdominal or intrapelvic organ, prostate biopsy, biopsy of tumors or otherwise suspected abnormal structures within the pelvis and abdomen, diagnosis of endometriosis, treatment by chemicals, cells, bio-agents, physical energy (e.g., cryo, radiofrequency, heat, laser) of any pathology within the pelvis and abdomen, visualization and application of therapy within the genitourinary tract, and drainage of abnormal or normal collection of fluid in actual or potential space in the abdomen, pelvis or genitourinary tract. In other embodiments, device 100 can be in the form of a catheter which can be used to drain fluid from a patient's gall bladder or any other hollow or solid organ in the abdomen.

Other procedures that can be performed using device 100 include procedures relating to diagnosis and treatment of infertility, including following a woman's ovum to determine an appropriate time for harvest, harvesting the ovum, and assisting in or performing the delivery of the fertilized egg to the uterus.

In some embodiments, device 100 can be designed for use in cardiac or vascular procedures and for accessing various targets. For example, device 100 can be designed to provide access to various structures such as the coronary sinus and other cardiac venous structures. Exemplary procedures that can be performed using device 100 can include: epicardial biopsy; electronic mapping (endocardial or epicardial); electromechanical mapping (endocardial or epicardial); endocardial or epicardial ablation using any form of energy; cannulation or delivery of catheters, pacing leads, and interventional devices; and mapping and access to the fossa ovalis and patent foramen ovale to enable crossing the atrial septum and allowing transvenous access to the left side of the heart; pericardiocentesis; left ventricular lead placement; delivery of therapy (e.g., drugs, stem cells, laser therapy, or ultrasound energy); epicardial coronary artery bypass; valve repair and placement, delivery of cardiac shape modifying devices (e.g., ACORN® or MYOSPLINT® devices); myocardial scar reconstruction; ventricular reconstruction; ventricular assist device placement; and the treatment by chemicals, cells, bio-agents, physical energy (e.g., cryo, radiofrequency, heat, laser) of any pathology within the pericardial space or myocardium or intracardiac. As such, device 100 can, in some cases, be in the form of a sheath-like device that is insertable through, for example, an incision in the patient's upper thigh and through a blood vessel all the way up to the heart. In such embodiments, guidewire can be provided within the device to guide the device to the target area. In other embodiments, for example as described herein with reference to, for example, FIGS. 1A, 1C, 1D, 3A, 3B, 6, and 11A the device can be inserted through the pericardial space through the use of an introducer needle integrated therein. In either case, device 100 could have one or more ultrasound transducers 210 disposed along its length to provide ultrasound imaging using the transducers 210.

In other embodiments, device 100 can be in the form of a device that is used in performing a cardiac procedure such as a biopsy instrument or an instrument for valve repair. In this case, device 100 can be provided with one or more transducers 210, along with the other components required to provide ultrasound imaging using the transducers 210 as discussed herein.

In other embodiments, device 100 can be in the form of devices for use in performing procedures on the musculoskeletal system and for accessing the musculoskeletal system. For example, device 100 can be used for treatment by chemicals, cells, bio-agents, or physical energy (cryo, radiofrequency, heat, laser) of any pathology within the joint cavity, joint components, or muscle and bone; visualization and application of therapy involving muscle, bone, and joint components, including a joint cavity; and drainage of abnormal or normal collection of fluid in actual or potential space in the muscle, bone, or joint components. In these embodiments, device 100 can be in the form of a catheter or sheath that provides access to the musculo-skeletal system, thus allowing therapy delivery, intervention, placement of devices and diagnostics. Device 100 can also be in the form of interventional devices for use in procedures on the musculo-skeletal system. Such catheters, sheaths, and devices are well known, and, thus, the general features of device 100 for these embodiments can be in accordance with conventional devices. Device 100 would further include one or more transducers 210, along with the other components required to provide ultrasound imaging using the transducers 210 as discussed herein.

In some embodiments, device 100 can be in the form of devices for use in procedures on the brain and nervous system and for accessing the brain and nervous system. For example, such devices can be used for the treatment by chemicals, cells, bioagents, or physical energy (cryo, radiofrequency, heat, laser) of any pathology within the cranium and spinal and peri-spinal space including the vasculature contained within; visualization and application of therapy within the cranium, spinal, and peri-spinal space and all contained vasculature; drainage of abnormal or normal collection of fluid in actual or potential space in the cranium, spinal, and peri-spinal space and all contained vasculature; and for transcatheter delivery of interventional devices such as aneurysm clips, hematologic treatments, and any other drug or non drug therapy, either directly or via the vasculature or via any other hollow structure within the cranium, spinal, and peri-spinal space and all contained vasculature. In these embodiments, device 100 can be in the form of a catheter or sheath that provides access to the brain and system, thus allowing therapy delivery, intervention, placement of devices and diagnostics.

Device 100 can further be adapted for use in procedures on the nasal passages, sinuses, and pharynx and for accessing the nasal passages, sinuses, and pharynx. In these embodiments, device 100 can be in the form of a catheter or sheath that provides access to a desired site of the nasal passages, sinuses, and pharynx, thus allowing therapy delivery, intervention, placement of devices and diagnostics. Device 100 can also be in the form of interventional devices for use in procedures on the nasal passages, sinuses, and pharynx (e.g., devices for therapy delivery, intervention, placement of devices and diagnostics). Such catheters, sheaths, and devices are well known, and, thus, the general features of device 100 for these embodiments can be in accordance with conventional devices. Device 100 would further include one or more transducers 210, along with the other components required to provide ultrasound imaging using the transducers 210 as discussed herein.

Device 100 can further be in the form of devices used to treat and address chronic problems and, as such, can be delivered and lodged in body cavities, organs, or other anatomic locations for long term monitoring or anatomy or function or dynamics including hemodynamics. In these examples, the device can be in the form of a catheter or sheath or other conventional chronic treatment or monitoring device that can be lodged at a desired site. Device 100 would further include one or more transducers 210, along with the other components required to provide ultrasound imaging using the transducers 210 as discussed herein.

In some embodiments, the present device 100 can further be integrated with other non-ultrasound imaging modalities including infrared, laser, optical coherence, fiber optic instruments including, but not limited to endoscopic mapping. For example, the body member 200 can further be provided with a fiber optic lumen through which an optical fiber is insertable.

The devices 100 can be used to perform any variety of medical procedures including those set forth herein. The general features of these procedures is in accordance with conventional procedures and further make use of the integrated imaging system to provide visualization while accessing and performing procedures at the target site.

Access to other organs, structures, and spaces can be performed in similar fashion with appropriate procedural modifications specific for the particular organs, structures or spaces.

All documents mentioned herein are incorporated by reference herein as to any description which may be deemed essential to an understanding of illustrated and discussed aspects and embodiments of devices and methods herein.

Although the devices and methods discussed above and primarily illustrated and described herein provide instruments that also can be adapted for performing minimally invasive diagnostic or therapeutic procedures on humans, it will be appreciated by those skilled in the art that such instruments and methods also are adaptable for use in other surgical procedures as well as in performing various veterinary surgeries. Further, while several preferred embodiments have been described using specific terms, such description is for illustrative purposes only, and it is to be understood that changes and variations may be made without departing from the spirit or scope of the following claims.

What is claimed is:

1. A device configured to be used in minimally invasive medical procedures, comprising:
    an elongate body having no exterior delivery catheter or sheath, the elongate body configured to facilitate entry of a catheter through skin tissue of a human body, the elongate body having proximal and distal ends, said elongate body having a tapered tip at the distal end being configured to be directly inserted into a target site within the human body during use of the device and having at least one longitudinal lumen extending along a longitudinal axis thereof;
    a first imaging element disposed in one of said at least one longitudinal lumen, said at least one longitudinal lumen having a proximal and a distal end, said first imaging element including a first ultrasound transducer being located at an outer periphery of the tapered tip of the elongate body at the distal end of the at least one longitudinal lumen, said first ultrasound transducer configured to provide a forward-directed imaging zone from the distal end to include the tapered tip of the elongate body, a distal tip of the tapered tip of the elongate body being a most distal portion of the elongate body and being forward of the first ultrasound transducer, the first ultrasound transducer being configured for forwardly guiding the device from a point of entry of the catheter through the tissue of the human body to the target site within the human body during use of the device;
    said first imaging element being configured to provide forward-directed imaging in a direction of the distal end of the elongate body to include the distal tip of the tapered tip of the elongate body; and
    a removable introducer needle disposed at an end-on aperture within the distal tip of the tapered tip of the elongate body during use of the device and being within said forward-directed imaging zone of said ultrasound transducer, said introducer needle and said device configured to be introduced into said human body substantially simultaneously during use of the device, said introducer needle being configured under ultrasound forward-directed imaging guidance, to puncture the human body proximate to said target site and to directly access and to puncture said target site including an internal body wall within the human body during use of the device via said forward-directed imaging zone of said ultrasound transducer.

2. The device according to claim 1, wherein said elongate body comprises a plurality of lumen and said first imaging element comprises a plurality of small ultrasound transducer elements arranged in a substantially cylindrical housing disposed in said one longitudinal lumen of said plurality of lumen.

3. The device according to claim 2, wherein said substantially cylindrical housing has a circular face at a distal end thereof and said plurality of small ultrasound transducer elements are arranged in a parallel row along a diameter of said circular face.

4. The device according to claim 2, wherein said substantially cylindrical housing has an elliptical face at a distal end thereof and said plurality of small ultrasound transducer elements are arranged in a parallel row along one of a major and a minor axis of said elliptical face.

5. The device according to claim 2, wherein said substantially cylindrical lousing has a flat face at a distal end thereof.

6. The device according to claim 2, wherein said substantially cylindrical housing has a rounded face at a distal end thereof.

7. The device according to claim 1, wherein said first ultrasound transducer is configured to operate at a frequency between 20 KHz and 300 MHz.

8. The device according to claim 7, wherein said first ultrasound transducer is configured to operate at a frequency less than 1 MHz to provide therapeutic treatment to the body during use of the device.

9. The device according to claim 7, wherein said first ultrasound transducer is configured to operate at a frequency above 1 MHz to provide forward-directed imaging within the body during use of the device.

10. The device according to claim 1, wherein said elongate body includes at least one transverse lumen extending in a transverse direction across a width of said elongate body, a second imaging element being disposed in said at least one transverse lumen.

11. The device according to claim 1, wherein said elongate body includes at least one transverse lumen extending in a transverse direction across a width of said elongate body, a fiber optic imaging element being disposed in one of said at least one longitudinal lumen and said at least one transverse lumen, said fiber optic imaging element being configured to provide imaging in one of a forward direction and of a transverse direction with respect to the elongate body.

12. The device according to claim 1, further comprising a microelectromechanical (MEMS) device operably attached to said first imaging element, said MEMS device being configured to permit manipulation of said first imaging element to control a direction of imaging provided by said first imaging element during use of the device in addition to said forward-directed imaging.

13. The device according to claim 1, further comprising a luer lock at the proximal end of the elongate body, said luer lock for connecting the introducer needle of the device to a syringe.

14. The device according to claim 1, further comprising a retrieval instrument disposed within a second one of said plurality of lumen, wherein said first imaging element is configured to provide forward-directed imaging guidance for operation of said retrieval instrument during use of the device.

15. The device according to claim 14, said retrieval instrument including a biopsy needle replacing said introducer needle.

16. The device according to claim 14, said retrieval instrument including a bioptome.

17. The device of claim 1 being configured for intracardiac treatment via pericardial access, the pericardial access without entry of the device through a blood vessel during use of the device.

18. A device configured to be used in minimally invasive medical procedures, comprising:
  an elongate body having no exterior delivery catheter or sheath configured to facilitate entry of a catheter through skin tissue of a human body, the elongate body having proximal and distal ends, said elongate body having a tapered tip at the distal end being configured to be directly inserted into a target site within the human body during use of the device, said elongate body having at least one longitudinal lumen extending along a longitudinal axis thereof and further having a plurality of detents along an outer surface thereof;
  a first imaging element disposed in one of said at least one longitudinal lumen, said first imaging element having a proximal and a distal end, said first imaging element including a first ultrasound transducer being located at an outer periphery of the tapered tip of the elongate body at the distal end of the at least one longitudinal lumen, said first imaging element being configured for forwardly guiding the device from a point of entry of the catheter into the tissue of the human body to the target site within the human body during use of the device and to provide forward-directed imaging during use of the device in a direction from the distal end to include the tapered tip of the elongate body, a distal tip of the tapered tip of the elongate body being a most distal portion of the elongate body and being forward of the first ultrasound transducer at the distal end;
  a removable introducer needle disposed within an end-on aperture within the distal tip of the tapered tip of the elongate body and within a further lumen extending through the elongate body, the introducer needle being within a forward-directed imaging zone of said ultrasound transducer during use of the device, said introducer needle and said device configured to be introduced into said human body substantially simultaneously during use of the device, said introducer needle being configured, under forward-directed ultrasound imaging guidance, to puncture an internal body wall proximate to said target site and to directly access said target site within the human body via said forward-directed imaging zone of said ultrasound transducer during use of the device; and
  an anchoring portion, said anchoring portion being slidably movable along a length of said elongate body and being further configured to lock into place at one of said plurality of detents to secure the device at a desired position within the human body during use of the device.

19. The device according to claim 18, said anchoring portion having at least one suture hole.

20. A device configured to be used in minimally invasive medical procedures, comprising:
  an elongate body having no exterior delivery catheter or sheath, the elongate body configured to facilitate entry of a catheter through skin tissue of a human body, the elongate body having proximal and distal ends, said elongate body having a tapered tip at the distal end, the elongate body being configured to be directly inserted into a target site within the human body during use of the device and having at least one longitudinal lumen extending along a longitudinal axis thereof, at least one of said at least one lumen having a groove extending along a length thereof;
  a removable introducer needle disposed within a forward-directed imaging zone of an ultrasound transducer, said introducer needle and said device configured to be introduced into said human body substantially simultaneously during use of the device, said introducer needle being configured, under ultrasound forward-directed imaging guidance, to puncture a human body wall proximate to said target site and to directly access said target site during use of the device, the introducer needle being disposed to extend from an end-on aperture of the tapered tip of the elongate body and being within said forward-directed imaging zone of said ultrasound transducer during use of the device; and
  a first imaging element, said first imaging element being disposed in a housing having a proximal and a distal end, said first imaging element including said ultrasound transducer at the distal end of said housing, said first imaging element being located at an outer periphery of the tapered tip of the elongate body and being configured to provide forward-directed imaging in a direction from the distal end of the elongate body to include a tip of the tapered tip of the elongate body, the tip being a most distal portion of the elongate body and being forward of said ultrasound transducer at the outer periphery of the tapered tip of the elongate body at the distal end of the elongate body, the first imaging element to provide imaging of forward navigation of the elongate body from a point of elongate body entry into the human body to a location proximate the target site within the human body during use;
  said housing having a ridge extending along a length thereof from said proximal to said distal end, said housing being configured for slidable insertion into said lumen having said groove, wherein said ridge on said housing joins with said groove in said lumen to provide a secure fit of said housing into said lumen.

21. The device of claim 20, further wherein said introducer needle is disposed in a second one of said at least one lumen, said needle being configured to facilitate access by the elongate body to a portion of the human body during use of the device.

22. A device configured to be used in minimally invasive medical procedures, comprising:
  an elongate body having no exterior delivery catheter or sheath configured to facilitate entry of a catheter through skin tissue of a human body, the elongate body having proximal and distal ends, said elongate body having a tapered tip at the distal end being configured to be directly inserted into a target site within the human body during use of the device and having a single longitudinal lumen extending along a longitudinal axis thereof;

a needle, said needle being situated within said single lumen in said elongate body, an end of said needle being configured to extend from an end-on aperture of the tapered tip of the elongate body at a most distal tip of said elongate body and being configured for puncturing a human body wall proximate to said target site and to directly access and to access said target site during use of the device, the distal tip and end-on aperture being a most distal portion of the elongate body; and a first imaging element, said first imaging element being disposed in a housing having a proximal and a distal end, said first imaging element including a first ultrasound transducer at the distal end of said housing, said first imaging element being located at an outer periphery of the tapered tip of the elongate body being configured to provide a forward-directed imaging zone for forward-directed imaging during use of said needle in a direction from the outer periphery of the tapered tip of the elongate body at the distal end to include the most distal tip of the elongate body and in a direction of said target site forward of said end-on aperture at said most distal tip during use of the device, said first imaging element being situated within said single lumen in said elongate body and said distal end of said housing of said first imaging element being separated from a proximal end of said needle by at least one buffer element, the first imaging element to provide imaging of forward navigation of the elongate body from a point of entry into the human body to the target site within the human body during use.

23. The device of claim 22, wherein said elongate body further includes at least one channel extending from the proximal end of the elongate body to a point beyond the at least one buffer element separating the first imaging element and the needle.

24. The device of claim 23, further including a Luer lock at a proximal end of the elongate body, the Luer lock being configured to attach to a syringe, said syringe being operably joined with said at least one channel and being configured to permit one of a delivery of fluid to said target site within the human body or a withdrawal of fluid from the target site via said needle during use of the device.

25. The device of claim 24, wherein said fluid configured to be delivered to the target site within the human body during use of the device includes one of a drug, a saline solution, or a contrast medium.

26. The device of claim 23, wherein said channel is configured to guide a guide wire from the proximal end of the elongate body to the distal end, said guide wire being configured to guide one of a second imaging element, a therapeutic device, an interventional device, or a diagnostic device to a target site within the human body during use of the device.

* * * * *